US010479826B2

United States Patent
Kalkum et al.

(10) Patent No.: US 10,479,826 B2
(45) Date of Patent: Nov. 19, 2019

(54) SINGLE CHAIN ANTIBODY DOMAINS FOR DETECTION OF ANTI-BOTULINUM NEUROTOXIN DOMAINS AND METHODS OF THEIR USE

(71) Applicant: CITY OF HOPE, Duarte, CA (US)

(72) Inventors: Markus Kalkum, Duarte, CA (US); Karine Bagramyan, Duarte, CA (US); Paul Yazaki, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/553,532

(22) PCT Filed: Feb. 29, 2016

(86) PCT No.: PCT/US2016/020094
§ 371 (c)(1),
(2) Date: Aug. 24, 2017

(87) PCT Pub. No.: WO2016/138526
PCT Pub. Date: Sep. 1, 2016

(65) Prior Publication Data
US 2018/0237507 A1    Aug. 23, 2018

Related U.S. Application Data

(60) Provisional application No. 62/121,642, filed on Feb. 27, 2015.

(51) Int. Cl.
*C07K 16/12* (2006.01)
*G01N 33/53* (2006.01)
*G01N 33/573* (2006.01)

(52) U.S. Cl.
CPC ..... *C07K 16/1282* (2013.01); *G01N 33/5308* (2013.01); *G01N 33/573* (2013.01); *C07K 2317/22* (2013.01); *C07K 2317/31* (2013.01); *C07K 2317/56* (2013.01); *C07K 2317/565* (2013.01); *C07K 2317/567* (2013.01); *C07K 2317/569* (2013.01); *C07K 2317/62* (2013.01); *C07K 2317/92* (2013.01); *G01N 2333/952* (2013.01)

(58) Field of Classification Search
None
See application file for complete search history.

(56) References Cited

U.S. PATENT DOCUMENTS

2013/0058962 A1  3/2013  Shoemaker et al.
2014/0294826 A1  10/2014  Shoemaker

OTHER PUBLICATIONS

Goldman "Enhancing stability of camelid and shark single domain antibodies: an overview" Front immun 8:865 (Year: 2017).*
Zebetakis "Contributions of the Complementarity Determining Regions to the Thermal Stability of a Sing-Domain Antibody" plos one 8(10): e77678 (Year: 2013).*
Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J Immunol 152(1):146-52 (Year: 1994).*
PCT/US2016/020094—International Search Report dated Sep. 2, 2016, 4 pages.
PCT/US2016/020094—Written Opinion dated Sep. 2, 2016, 4 pages.
Inoue, H, et al., Affinity Transfer to a Human Protein by CDR3 Grafting of Camelid VHH, Protein Science, Oct. 5, 2011, vol. 20, No. 12, pp. 1971-1981.
Poul, Ma et al., Inhibition of T Cell Activiation with a Humanized Anti-beta 1 Integrin Chain mAb, Molecular Immunology, Feb. 1995, vol. 32, No. 2, pp. 101-116.
Anti-CD29 antibody heavy chain variable region, partial [*Mus* sp.], National Center for Biotechnology Information, Genbank Entry Accessaion No. AAB33498, Feb. 1995 [retrieved on Jul. 27, 2016], retrieved from the internet http://ncbi.nlm.nih.gov/protein/914124/, pp. 1-2.

* cited by examiner

*Primary Examiner* — Adam Weidner
(74) *Attorney, Agent, or Firm* — Mintz, Levin, Cohn, Ferris, Glovsky and Popeo, P.C.

(57) ABSTRACT

Provided herein, inter alia, are single chain antibody binding domains (VHHs) for use in conjunction with the Assay with a Large Immuno-sorbent Surface Area (ALISSA). Engineered and affinity matured VHHs are used as affinity reagents in the ALISSA resulting in an exceptionally sensitive and precise method for the detection of toxins at miniscule concentrations. Thus, provided herein are methods as well as reagents that can be used to detect the presence of botulinum neurotoxins in quantities well below 1 pg/mL which corresponds to a lethal concentration under presumed equal distribution throughout the human body.

18 Claims, 6 Drawing Sheets

Specification includes a Sequence Listing.

$y = 5 \times 10^{11} X^{0.4615}$
$R^2 = 0.9896$

LOQ = 24.5 aM

[BoNT/A holotoxin], mol/L

SINGLE CHAIN ANTIBODY DOMAINS FOR DETECTION OF ANTI-BOTULINUM NEUROTOXIN DOMAINS AND METHODS OF THEIR USE

CROSS-REFERENCE TO RELATED APPLICATIONS

This application claims priority to International Application No. PCT/US2016/020094, filed Feb. 29, 2016, which claims priority to U.S. Provisional Patent Application No. 62/121,642, filed Feb. 27, 2015, the disclosures of which are incorporated by reference herein in its entirety.

GOVERNMENT INTEREST

The invention was made with government support under 5R01 AI096169 awarded by the National Institutes of Health. The government has certain rights in the present invention.

REFERENCE TO A "SEQUENCE LISTING," A TABLE, OR A COMPUTER PROGRAM LISTING APPENDIX SUBMITTED AS AN ASCII FILE

The Sequence Listing, created Aug. 10, 2017, 26,092 bytes, machine format IBM-PC, MS Windows operating system, is hereby incorporated by reference.

FIELD OF INVENTION

Disclosed herein, inter alia, are methods and reagents for enhanced sensitivity in detecting Botulinum neurotoxins in biological samples.

BACKGROUND

Botulinum neurotoxins (BoNTs) are important medical agents, used to treat dystonias, blepharospasms, hyperhidrosis and other neurological diseases. However, BoNTs also represent some of the most toxic substances known to man and their potential abuse as a threat agent is feared (Arnon, et al. 2001; Wein, L. M. & Liu, Y., 2005). The detection of Botulinum neurotoxin (BoNT) in complex samples such as foods or clinical specimens represents an analytical challenge. The current "gold standard" in the art for detecting BoNT is the mouse toxicity assay, which can detect as little as 10 pg BoNT (Ferreira, J. L., et al., 2003). However, BoNT can be lethal to humans in systemic doses as low as 1 to 2 ng/Kg body weight (Arnon Id.). Therefore, there is a pressing need for more sensitive assays for detecting the presence of BoNT in a sample.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

In a first aspect, there is provided a method for detecting the presence of a botulinum toxin in a sample. The method includes a) exposing the sample containing a botulinum toxin to (i) an anti-botulinum neurotoxin camelid-derived single chain antibody binding domain (VHH) and (ii) a detectable toxin substrate, thereby forming a detectable toxin substrate-VHH complex. The method further includes b) detecting the detectable toxin substrate-VHH complex.

In another aspect, there is provided a single chain antibody binding domain (VHH) including the amino acid sequence set forth in SEQ ID NO:3.

In another aspect, there is provided a nucleic acid encoding the VHH set forth in SEQ ID NO:3.

In another aspect, there is provided a vector including the nucleic acid encoding the VHH set forth in SEQ ID NO:3.

In another aspect, there is provided a cell including the vector including the nucleic acid encoding the VHH set forth in SEQ ID NO:3.

In another aspect, there is provided a multimeric VHH construct comprising an N-terminal first VHH and a C-terminal second VHH, wherein the first VHH and the second VHH are independently any affinity matured VHH disclosed herein or a VHH comprising a CDR1 GFGTWFRFDENT (SEQ ID NO:14), CDR2 VARYPKSGIV (SEQ ID NO: 15) or CDR3 NVGEF (SEQ ID NO: 16), wherein at least one of the first VHH or the second VHH are any affinity matured VHH disclosed herein.

In another aspect, there is provided a multimeric single chain antibody binding domain (VHH) construct including the amino acid sequences set forth in SEQ ID NO:1, SEQ ID NO:3 and SEQ ID NO:3.

In another aspect, there is provided a nucleic acid encoding the multimeric VHH construct as described herein.

In another aspect, there is provided a vector including the nucleic acid encoding the multimeric VHH construct as described herein.

In another aspect, there is provided a cell including the vector including the nucleic acid encoding the multimeric VHH construct as described herein.

In another aspect, there is provided a kit including: a) an anti-botulinum neurotoxin camelid-derived single chain antibody binding domain (VHH) and; b) a detectable toxin substrate.

In another aspect, there is provided a pharmaceutical composition including (a)(i) an anti-botulinum neurotoxin camelid-derived single chain antibody binding domain (VHH) as described herein or (ii) a multimeric VHH construct as described herein; and (b) one or more pharmaceutically acceptable carriers.

In another aspect, there is provided a method for treating botulism in an individual in need thereof. The method includes administering a therapeutically effective amount of (a) an anti-botulinum neurotoxin camelid-derived single chain antibody binding domain (VHH) as described herein, (b) a multimeric VHH construct as described herein, or (c) a pharmaceutical composition as described herein to the individual.

Each of the aspects and embodiments described herein are capable of being used together, unless excluded either explicitly or clearly from the context of the embodiment or aspect.

BRIEF DESCRIPTION OF THE DRAWINGS

FIG. 2. The figure depicts a dilution series of BoNT/A holotoxin and ALISSA response (in ARFU). The LOQ (i.e., limit of quantitation) was deduced using the method described by Armbruster D A & Pry T (THE CLINICAL BIOCHEMIST REVIEWS, 2008, v29).

FIG. 4A and FIG. 4B. The figure depicts comparison of amino acid sequence, sense and anti-sense DNA sequences, and molecular features of the *E. coli* codon optimized H7*-H7*-C2 heterotrimer in pET28.

DETAILED DESCRIPTION

Figure 1:
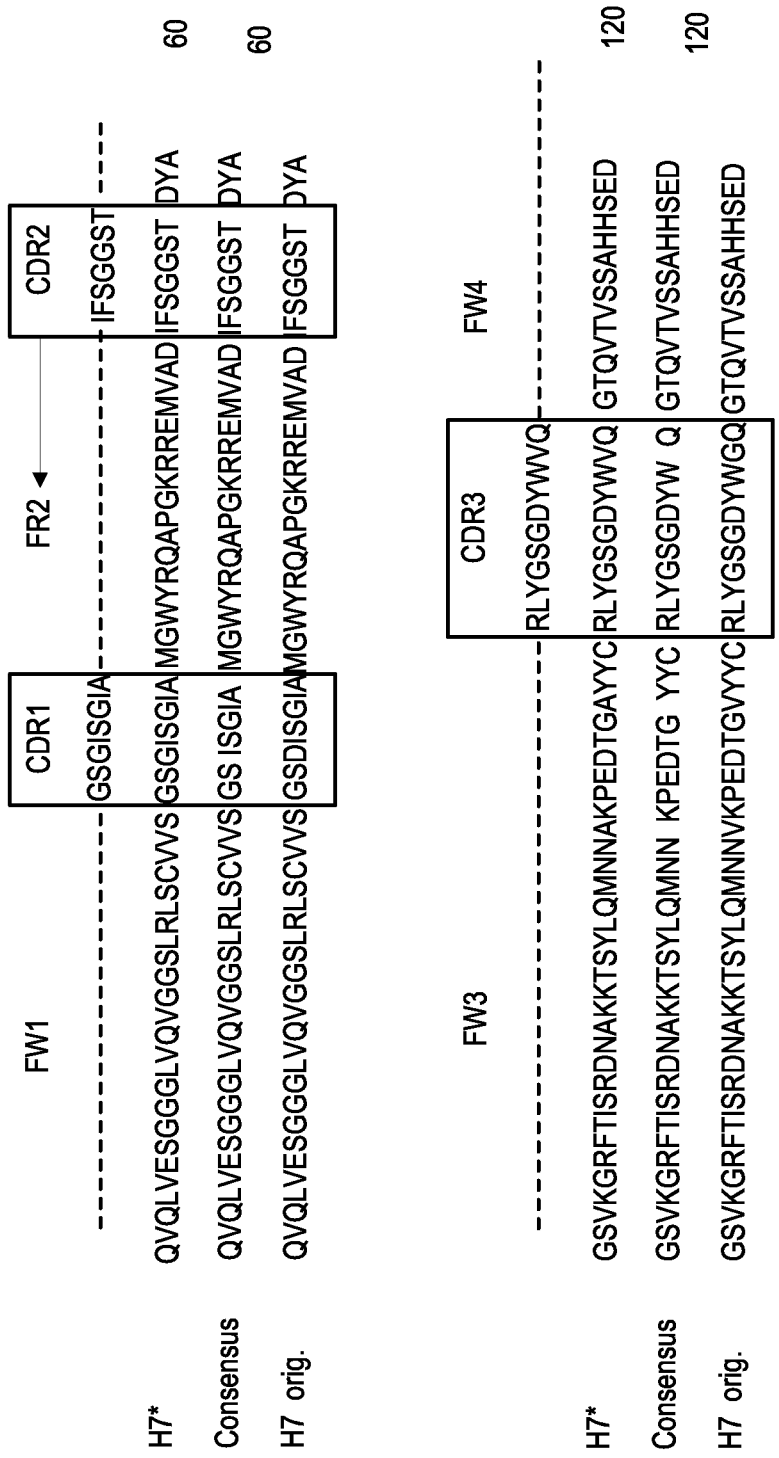
FIG. 1. The figure depicts sequence comparison of the polypeptide of the affinity matured H7* with its original H7 VHH. The consensus sequence, CDRs, and framework (FW) regions are also depicted. The sequences differ by four amino acids. The corresponding DNA sequences are entirely different, because each codon was optimized for protein expression in *E. coli* (see FIG. 4). Sequence legend: H7*; consensus; H7 orig.

Even at very low systemic doses of 1 to 2 ng/kg body weight, botulinum toxin (BoNT) can be lethal to humans (Arnon 2001). Unfortunately, detection of BoNT at these low but deadly levels is difficult using conventional means. For example, in infant botulism (IB), a condition in which a baby's intestines have become colonized by toxin-secreting *Clostridium botulinum* bacteria, it is possible to detect BoNT in stool samples (Arnon 2006). However, attempts to diagnose IB serologically via detection of BoNT in the blood have been deemed unreliable (Schantz 1992). Nevertheless, the systemic presence of the toxin in IB cannot be disputed, because of its apparent quick distribution throughout the infant's entire body, by which it efficiently shuts down motor neurons distant from the intestinal source. The resulting symptoms can include complete paralysis, respiratory failure, and if left untreated, death. Except for PCR-based assays, most assays are not well suited to provide the desired detection of less than 1 pg/mL BoNT in a complex sample. By approximation, 1 pg/mL corresponds to the lethal concentration under presumed equal distribution throughout the human body.

The invention described herein provides, inter alia, single chain antibody binding domains (VHHs) for use in conjunction with the Assay with a Large Immuno-sorbent Surface Area (ALISSA). In embodiments, the use of engineered and affinity matured VHHs as affinity reagents in the ALISSA results in an exceptionally sensitive and precise method for the detection of BoNT even at extremely low concentrations. Thus, in embodiments, methods as well as reagents are provided herein that can be used to detect the presence of this particularly deadly neurotoxin in quantities well below the 1 pg/mL concentration that conventional BoNT detection methods have thus far been unable to consistently achieve. As such, embodiments herein provide an important public health benefit for diagnosing and detecting this toxin in individuals and in the environment, respectively. Additionally, provided herein are ALISSA-suitable VHH high affinity reagents that can be inexpensively produced in bacteria. In embodiments, the VHH high affinity reagents are readily anchored onto support matrices on which they will assume the correct and desired orientation for performance of the ALISSA.

Definitions

As used herein, the term "protein" includes polypeptides, peptides, fragments of polypeptides, and fusion polypeptides.

As used herein, a "nucleic acid" refers to two or more deoxyribonucleotides and/or ribonucleotides covalently joined together in either single or double-stranded form.

As used herein, the term "ALISSA" (Assay with a Large Immuno-sorbent Surface Area) refers to a previously described method for detecting the activity of a toxin or enzyme. The method employs common lab equipment and commercially available reagents, and is therefore expected to be reproducible by any reasonably well equipped biological laboratory. In certain embodiments, the ALISSA is employed for the detection of botulinum toxin A (BoNT/A). For example, exemplary experimental results have shown that the assay can detect less than 0.5 fg of BoNT/A holotoxin in 1 mL serum, milk, or GP-diluent. Based on these results, the ALISSA is at least about 32,000-fold more sensitive than the live mouse assay and about 160,000-fold more sensitive than the Enzyme-linked Immunosorbent Assay (ELISA).

As used herein, the term "target" when used to refer to a toxin or enzyme, is used to refer to any chemical, biochemical or biological species or compound that is known or referred to in the art as a toxin or an enzyme. A target toxin or target enzyme includes those compounds having proteolytic, catalytic or enzymatic activity. A target toxin or target enzyme includes those compounds able to modify a substrate so as to alter or change the substrate's chemical structure or apparent structure or activity. For example, a botulinum neurotoxin type A is a "target" toxin that has proteolytic activity and is able to cleave its specific substrates. As another example, a chitinase is a "target" enzyme that has enzymatic activity.

As used herein, the term "substrate" is used to refer to any chemical, biochemical or biological species or compound that complex with, reacts, with, is capable of being modified by, or otherwise interacts with a toxin or enzyme having bioactivity. For example, a botulinum type toxin is a protease able to enzymatically cleave specific protein substrates such as synaptic membrane proteins, SNARE proteins or SNAP-25 proteins. As another example, a chitinase substrate interacts with a chitinase enzyme such as endochitinase or exochitinase.

As used herein, the term "fluorogenic substrate," and "fluorophore" may be used interchangeably to describe a substrate that is hydrolyzed by or otherwise reacted with a target toxin upon contact therewith, producing a complex, product or other derivative thereof which liberates fluorescence upon excitation by a suitable light source.

As used herein the term "bioluminescent substrate," "luminescent substrate," and "luminogenic" protein may be used interchangeably to describe a substrate that is activated by or otherwise interacts or reacts with a target toxin upon contact therewith, producing a complex, product, or other derivative thereof which emits light at distinct wavelengths suitable for detection as desired.

The term "VHH" refers to single chain antibody binding domains devoid of light chains. Preferably a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. Said VHH may be a natural VHH, such as a Camelid-derived VHH, or a recombinant protein comprising a heavy chain variable domain. In some embodiments, the VHH is derived from a species selected from the group consisting of camels, llamas, vicuflas, guanacos, and cartilaginous fish (such as, but not limited to, sharks). In another embodiment, the VHH is derived from an alpaca (such as, but not limited to, a Huacaya Alpaca or a Suri alpaca).

"Natural BoNT" typically resides within ~300, 500 or 900-kDa protein complexes together with other non-toxic components, the neurotoxin associated proteins (NAPs) (Sakaguchi 1982; Chen 1998; Sharma 2003; Melling 1988; Zhang 2003; Aoki 2001). Several structurally distinct serotypes of BoNT (types A to G) have been discovered. BoNT Type A (BoNT/A) (CAS Registry Number: 93384-43-1) is most prevalent in the Western United States (Smith 1978) and is causatively involved in approximately 60% of the IB cases in California (the rest being mostly attributed to type B) (Amon 2001). The toxin itself is a 150-kDa zinc-binding metalloprotease that, following expression, is endogenously cleaved into a 100-kDa heavy and a 50-kDa light chain connected by a reducible disulphide bond (Schiavo 2000) and by a belt-like extension of the heavy chain that loops around the light chain (Lacy 1998). The catalytic site is located on the light chain (Kurazono 1992). Reduction of the chain-bridging disulphide bond exposes the catalytic site and enhances its activity (Lacy 1998), also referred to as "activation" of the toxin by some authors and toxin manufacturers (Cai 1999; Cai 2001). The potency of BoNT results from its ability to cleave on or more of the three SNARE proteins involved in fusing acetylcholine-containing synaptic vesicles with terminal motor neurons membrane, triggering muscle contraction (Shiavo 2000).

An "individual" can be a vertebrate, a mammal, or a human. Mammals include, but are not limited to, farm animals, sport animals, pets, primates, mice and rats. In embodiments, an individual is a human.

"Treatment," "treat," or "treating," as used herein covers any treatment of a disease or condition of an individual and includes, without limitation: (a) preventing the disease or condition from occurring in an individual which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of individuals treated by the methods of the invention includes individuals suffering from the undesirable condition or disease, as well as individuals at risk for development of the condition or disease. In embodiments, the disease or condition is botulism.

Unless defined otherwise herein, all technical and scientific terms used herein have the same meaning as commonly understood by one of ordinary skill in the art to which this invention pertains.

As used herein, the singular terms "a." "an," and "the" include the plural reference unless the context clearly indicates otherwise.

Compositions of the Invention
Single Chain Antibody Binding Domains

A single chain antibody binding domains (e.g. "Nanobody®") is an antibody fragment containing a single monomeric variable antibody domain. Similar to conventional whole antibodies, they are able to bind selectively to a specific antigen. With molecular weights typically only 12-15 kDa, single chain antibody binding domains are usually much smaller than conventional antibodies (150-160 kDa) which are composed of two heavy protein chains and two light chains. Single chain antibody binding domains are typically smaller than Fab fragments (~50 kDa, one light chain and half a heavy chain) as well as single-chain variable fragments (~25 kDa, two variable domains, one from a light and one from a heavy chain).

The first single chain antibody binding domains were engineered from heavy-chain antibodies found in camelids and were called VHH fragments. Cartilaginous fish also have heavy-chain antibodies ("immunoglobulin new antigen receptors" (IGNARs)), from which single-domain antibodies called VNAR fragments can be obtained. Single-domain antibodies are typically peptide chains of about 110 amino acids long, comprising one variable domain (VH) of a heavy-chain antibody, or of a common IgG. These peptides have similar affinity to antigens as whole antibodies, but are more heat-resistant and stable towards detergents and high concentrations of urea.

Figure 4A:
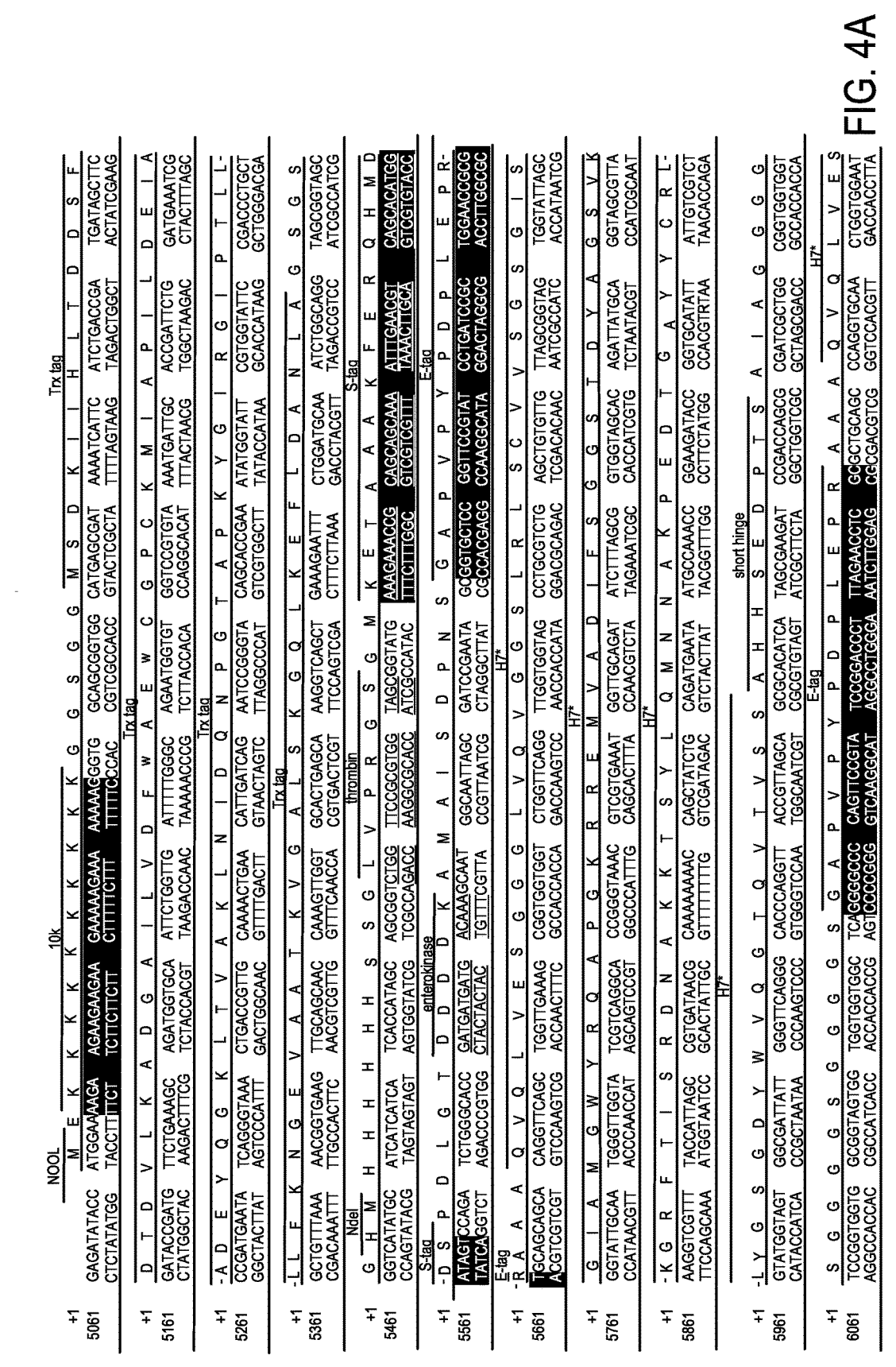
Figure 4B:
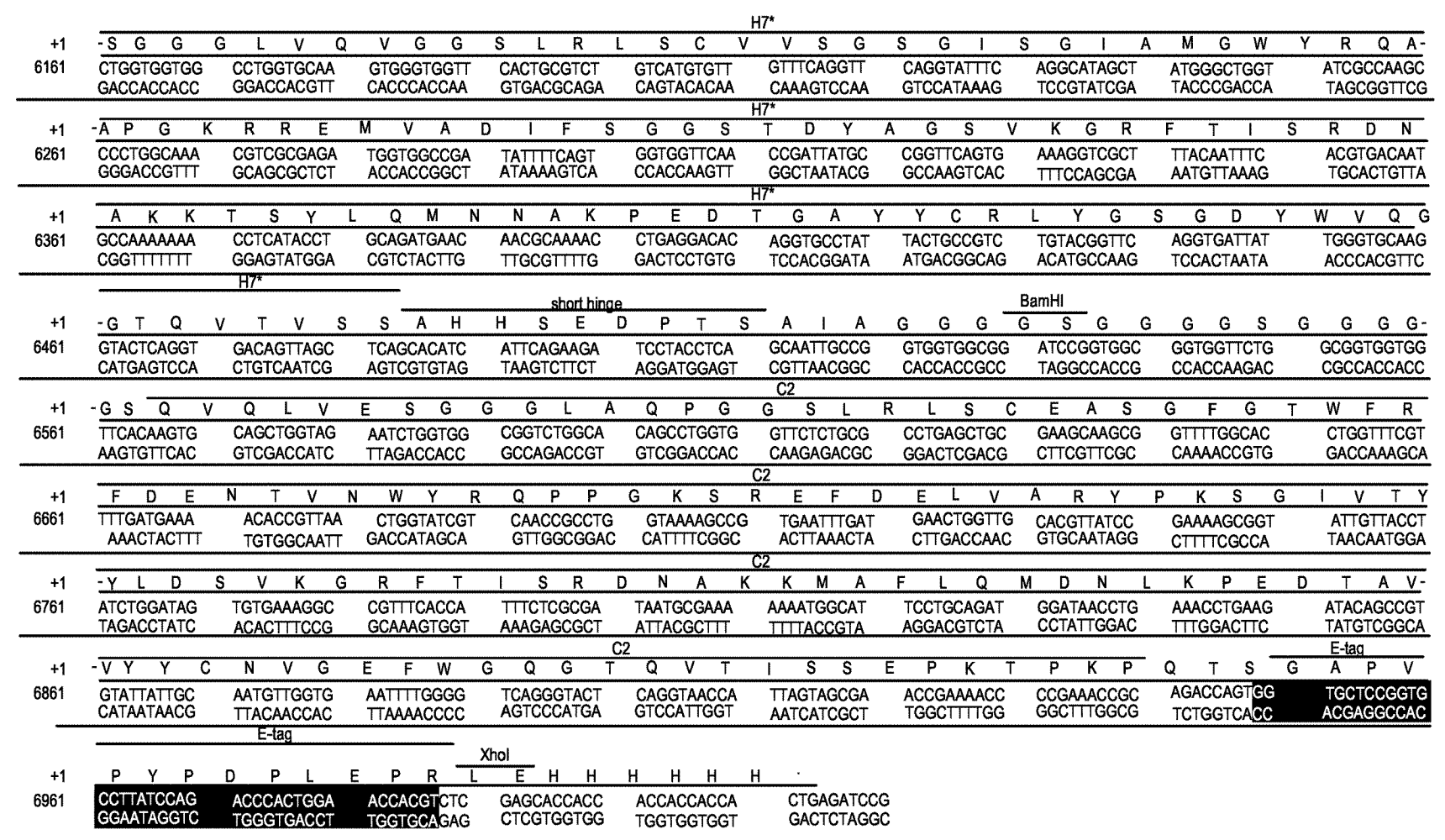

In some aspects, the present invention relates to binding agents that are specific to the microbial neurotoxin that causes botulism. There are at least seven different botulinum toxin serotypes (A to G), sometimes with various isotypes, and many of these different toxins can cause human disease. As described in the Examples section, several binding agents specific to botulinum neurotoxin serotype A were made. Hence, the methods and systems of the present invention include binding agents that have binding regions specific to one or more target areas of one or more neurotoxins involved with botulism. Sequences engineered to bind to this neurotoxin are shown in FIGS. 1 and 4. Specifically, the present invention relates to VHH binding agents having the amino acid sequence of SEQ ID NOs: 1, 2, and 3. Similarly, the present invention also includes VHH binding agents that are encoded by the nucleic acid sequence of SEQ ID NO: 4.

In embodiments, the VHH binding agents disclosed herein have one, two, or three complementarity determining regions (CDRs). As shown in FIG. 1, CDR1 of the VHH binding agent can comprise the amino acid sequence GSGISGIA (SEQ ID NO:5); CDR2 of the VHH binding agent can comprise the amino acid sequence IFSGGST (SEQ ID NO:6); and CDR3 of the VHH binding agent can comprise the amino acid sequence RLYGSGDYWVQ (SEQ ID NO:7). In embodiments, the VHH binding agent comprises the CDR sequences of SEQ ID NO:5. SEQ ID NO:6, and SEQ ID NO:7.

In embodiments, the VHH binding agents disclosed herein have one, two, three, or four framework (FW) regions. As shown in FIG. 1, FW1 of the VHH binding agent can comprise the amino acid sequence QVQLVES-GGGLVQVGGSLRLSCVVS (SEQ ID NO:8); FW2 of the VHH binding agent can comprise the amino acid sequence MGWYRQAPGKRREMVAD (SEQ ID NO:9); FW3 of the VHH binding agent can comprise the amino acid sequence GSVKGRFTISRDNAKKTSYLQMNNAKPEDTGAYYC (SEQ ID NO: 10); and FW4 of the VHH binding agent can comprise the amino acid sequence GTQVTVSSAHHSED (SEQ ID NO: 11). In embodiments, the VHH binding agent comprises the FW sequences of SEQ ID NO:8, SEQ ID NO:9, SEQ ID NO: 10, and SEQ ID NO: 11. In embodiments, one or more of the FW sequences of SEQ ID NO:8, SEQ ID NO:9, SEQ ID NO:10, and SEQ ID NO:11 have one or more conservative amino acid substitutions.

Further to any aspect or embodiment disclosed herein, in embodiments the VHH comprises the amino acid sequence QVQLVESGGGLAQPGGSLRLSCEASGFGTWFRFDE-NTVNWYRQPPGKSREFDELVARYPKSGIVTYLDSVK- GRFTISRDNAKKMAFLQMDNLKPEDTAVYYCNVGE-FWGQG TQVTISSEPKTPKP (SEQ ID NO:1). In embodiments, the VHH comprises the amino acid sequence QVQLVESGGGLVQVGGSLRLSCVVSGSDISGIAMG-WYRQAPGKRREMVADIFSGGS TDYAGSVKGRFTIS-RDNAKKTSYLQMNNVKPEDTGVYYCRLYGSGDY-WGQGTQVT VSSAHHSED (SEQ ID NO:2). In embodiments, the amino acid sequence of SEQ ID NO: 1 or SEQ ID NO:2 have one or more conservative amino acid substitutions. In some embodiments, the VHH binds to BoNT with a dissociation constant ($K_d$) of between about of 30-100 pM. In some embodiments, the VHH binds to BoNT with a dissociation constant ($K_d$) of between about 35-90 pM. In some embodiments, the VHH binds to BoNT with a dissociation constant ($K_d$) of between about 40-80 pM. In some embodiments, the VHH binds to BoNT with a dissociation constant ($K_d$) of between about 45-70 pM. In some embodiments, the VHH binds to BoNT with a dissociation constant ($K_d$) of between about 50-60 pM. In some embodiments, the VHH binds to BoNT with a dissociation constant ($K_d$) of less than about 90 pM. In some embodiments, the VHH binds to BoNT with a dissociation constant ($K_d$) of less than about 80 pM. In some embodiments, the VHH binds to BoNT with a dissociation constant ($K_d$) of less than about 70 pM. In some embodiments, the VHH binds to BoNT with a dissociation constant ($K_d$) of less than about 60 pM. In other embodiments, the VHH binds to BoNT with a dissociation constant ($K_d$) of less than about 50 pM. In some embodiments, the VHH binds to BoNT with a dissociation constant ($K_d$) of less than about 40 pM. In some embodiments, the VHH binds to BoNT with a dissociation constant ($K_d$) of less than about 30 pM.

Further to any aspect or embodiment disclosed herein, any of the VHH-containing constructs (including the multimeric. e.g., heterotrimeric, VHH-containing constructs) disclosed herein can contain one or more amino acid substitutions in either or both of the construct's CDR domains or FW regions to produce a polypeptide variant. These polypeptide variants retain the binding characteristics of the VHH-containing constructs (such as the ability to bind BoNT) but differ in amino acid sequence by any of 1, 2, 3, 4, 5, 6, 7, 8, 9, or 10 or more amino acids relative to the amino acid sequence of the parent VHH-containing construct. In embodiments, the amino acid sequence of SEQ ID NO:1 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:2 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:3 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:5 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:6 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:7 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:8 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:9 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO: 10 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:11 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO: 14 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:15 can differ in amino acid sequence by any of 1, 2, 3, 4, 5, 6, 7, 8, 9, or 10 or more amino acids (e.g., by one or more conservative amino acid substitutions) relative to the amino acid sequence of the parent. In embodiments, the amino acid sequence of SEQ ID NO:16 can differ in amino acid sequence by any of 1, 2, 3, 4, 5, 6, 7, 8, 9, or 10 or more amino acids (e.g., by one or more conservative amino acid substitutions) relative to the amino acid sequence of the parent. As known in the art, a desired amino acid sequence encoding a VHH polypeptide variant can be determined using methods known in the art and a nucleic acid sequence encoding such amino acid sequence variant can be generated synthetically using well-known recombinant DNA technology.

The amino acid sequence of the parent VHH polypeptide can be modified in order to generate a variant with altered binding affinity or activity in vitro and/or in vivo. Generally, the modification entails one or more amino acid substitutions. In embodiments, the replacement residue does not correspond to a residue present in the same position in any native VHH sequence. In the case of an amino acid substitution, the present invention contemplates replacement of the residue of the parent polypeptide with any other amino acid residue. The substitution may, for example, be a "conservative substitution." Such conservative substitutions are shown in Table 1 under the heading of "preferred substitution." More substantial changes may be achieved by making one or more "exemplary substitutions" which are not the preferred substitution in Table 1.

TABLE 1

| Original Residue | Exemplary Substitutions | Preferred Substitution |
| --- | --- | --- |
| Ala (A) | val; leu; ile | Val |
| Arg (R) | lys; gln; ssn | Lys |
| Asn (N) | gln; his; lys; arg | Gln |
| Asp (D) | glu | Glu |
| Cys (C) | ser | Ser |
| Gln (Q) | asn | Asn |
| Glu (E) | asp | Asp |

TABLE 1-continued

| Original Residue | Exemplary Substitutions | Preferred Substitution |
|---|---|---|
| Gly (G) | pro; ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

In other embodiments, the VHH can undergo affinity maturation to improve its binding capabilities. An "affinity-matured" VHH has one or more alterations that CDR which result in an improved affinity for a target antigen (such as BotN), as compared to the respective "parent" VHH. Affinity-matured VHHs of the invention may be prepared by methods known in the art, for example, as described by Marks et al., 1992, Biotechnology 10:779-783, or Barbas, et al., 1994, Proc. Nat. Acad. Sci, USA 91: 3809-3813; Shier et al., 1995, Gene 169:147-155; Yelton et al., 1995, Immunol. 155: 1994-2004; Jackson et al., 1995. J. Immunol. 154(7):3310-9; and Hawkins et al., 1992, J. Mol. Biol. 226(3): 889 896; K S Johnson and R E Hawkins, "Affinity maturation of antibodies using phage display," Oxford University Press 1996.

Further to any aspect or embodiment disclosed above, in embodiments the VHH is an affinity matured VHH and comprises the amino acid sequence QVQLVESGGGL-VQVGGSLRLSCVVSGSGISGIAMGWYRQAPGKRRE-MVADIFSGGSTDYAGSVKGRFTISRDNAKKTSYLQM-NNAKPEDTGAYYCRLYGSGDYWVQGTQVT VSSAH-HSED (SEQ ID NO:3). In some embodiments, the affinity matured VHH binds to BoNT with a dissociation constant ($K_d$) of less than about 90 pM. In some embodiments, the affinity matured VHH binds to BoNT with a dissociation constant ($K_d$) of less than about 80 pM. In some embodiments, the affinity matured VHH binds to BoNT with a dissociation constant ($K_d$) of less than about 70 pM. In some embodiments, the affinity matured VHH binds to BoNT with a dissociation constant ($K_d$) of less than about 60 pM. In other embodiments, the affinity matured VHH binds to BoNT with a dissociation constant ($K_d$) of less than about 50 pM. In some embodiments, the affinity matured VHH binds to BoNT with a dissociation constant ($K_d$) of less than about 40 pM. In some embodiments, the affinity matured VHH binds to BoNT with a dissociation constant ($K_d$) of less than about 30 pM. In some embodiments, the affinity matured VHH binds to BoNT with a dissociation constant ($K_d$) of less than about 20 pM. In other embodiments, the affinity matured VHH binds to BoNT with a dissociation constant ($K_d$) of at least about 12 pM. In embodiments, the amino acid sequence of SEQ ID NO: 3 has one or more conservative amino acid substitutions.

Further information related to VHHs specific to BoNT can be found in U.S. Patent Application Publication No. 2011/0129474, the disclosure of which is incorporated by reference herein in its entirety.

Multimeric Single Chain Antibody Binding Domains

Figure 3:
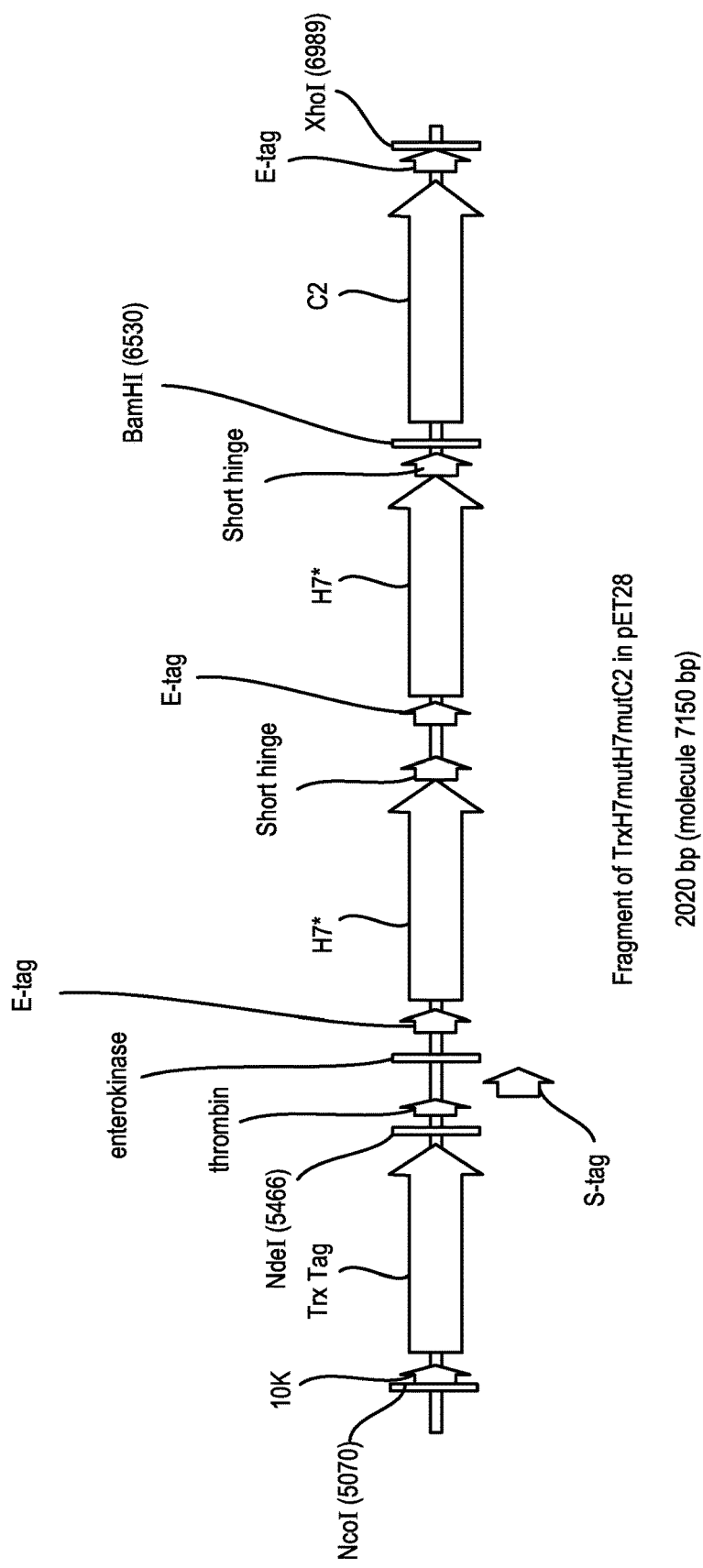
FIG. 3. The figure depicts in schematic form a feature map of the H7*-H7*-C2 heterotrimer in pET28. Trx is a thioredoxin tag that stemmed from an original pET32 vector. The spacer between the Trx tag and the first H7* contains 74 amino acids, including a thrombin cleavage site, an S-tag, an enterokinase cleavage site, and an E-tag. The spacer between the two H7* VHHs is 43 amino acids long. It includes a VHH short hinge and and E-tag. The spacer between the H7* and C2 VHHs is 27 amino acids long.
Figure 5:
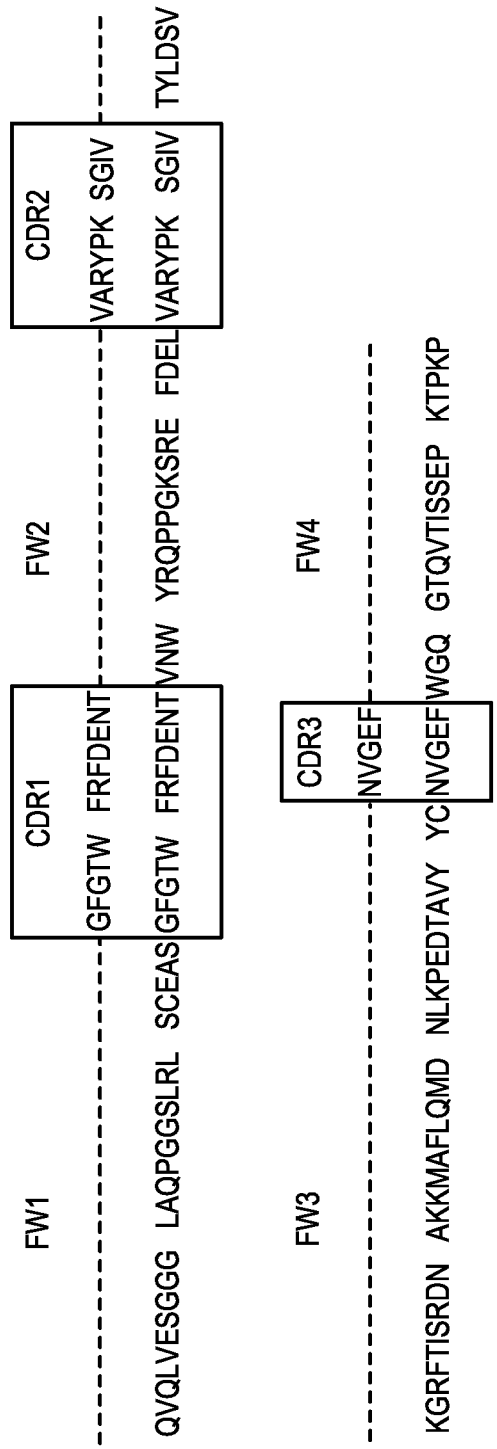
FIG. 5. The figure depicts the sequence of the C2 polypeptide. The consensus sequence, CDRs, and framework (FW) regions are also depicted.

Additionally, the present invention encompasses multimeric VHHs having two or more monomers wherein the monomer comprises a VHH sequence, such as any of those recited herein. Accordingly, in one embodiment, a multimeric binding agent includes two or more VHH (such as, but not limited to, any of 2, 3, 4, 5, or more) sequences described herein in a single binding agent. Any combination of two or more VHH sequences can form a multimeric binding agent of the present invention. In a particular embodiment, the present invention relates to a heterotrimeric VHH in which three different VHH sequences (such as any of those described herein) are fused together. A non-limiting representative example of such a heterotrimeric VHH is schematically depicted in FIG. 3 as well as depicted by amino acid and nucleotide sequence in FIG. 4.

In some embodiments, the multimeric VHH is a dimeric VHH construct comprising two copies of SEQ ID NO: 1; two copies of SEQ ID NO:2; or two copies of SEQ ID NO:3. In another embodiment, the multimeric VHH construct is a heterodimeric VHH construct comprising SEQ ID NO:1 and SEQ ID NO:2; SEQ ID NO:2 and SEQ ID NO:3; or SEQ ID NO:1 and SEQ ID NO:3. In yet another embodiment, the multimeric VHH construct is a heterotrimeric VHH construct comprising two copies of SEQ ID NO: 1 and one copy of SEQ ID NO:2; two copies of SEQ ID NO:1 and one copy of SEQ ID NO:3; two copies of SEQ ID NO:2 and one copy of SEQ ID NO: 1; two copies of SEQ ID NO:2 and one copy of SEQ ID NO:3; two copies of SEQ ID NO:3 and one copy of SEQ ID NO: 1; two copies of SEQ ID NO:3 and one copy of SEQ ID NO:2, or one copy each of SEQ ID NO:1, SEQ ID NO:2, and SEQ ID NO:3. In embodiments, the multimeric VHH construct is a dimeric VHH construct comprising two VHH domains connected by a linker. The linker may be in some embodiments a third VHH separated from the first two VHH domains by a first peptide linker and a second peptide linker.

Further to any aspect or embodiment disclosed herein, in embodiments the VHH is a heterotrimeric VHH comprising the amino acids QVQLVESGGGLAQPGGSLRLSCEAS-GFGTWFRFDENTVNWYRQPPGKSREFDELVA RYPK-SGIVTYLDSVKGRFTISRDNAKKMAFLQMDNLKPE-DTAVYYCNVGEFWGQG TQVTISSEPKTPKP (SEQ ID NO:1), QVQLVESGGGLVQVGGSLRLSCVVSGSGISGI-AMGWYRQAPGKRREMVADIFSGGS TDYAGSVKGR-FTISRDNAKKTSYLQMNNAKPEDTGAYYCRLYGSG-DYWVQGTQVT VSSAHHSED (SEQ ID NO:3), and QV-QLVESGGGLVQVGGSLRLSCVVSGSGISGIAMGWY-RQAPGKRREMVADIFSGGS TDYAGSVKGRFTISRDN-AKKTSYLQMNNAKPEDTGAYYCRLYGSGDYWVQG-TQVT VSSAHHSED (SEQ ID NO:3). In embodiments, the heterotrimeric VHH construct binds to BoNT with a Limit of Quantification (LOQ) of at least about 75, 70, 65, 60, 55, 50, 45, 40, 39, 38, 37, 36, 35, 34, 33, 32, 31, 30, 29, 28, 27, 26, 25, 24, 23, 22, 21, 20 attomolar (aM), or less, inclusive of inclusive of values occurring in between these numbers. In another embodiment, the heterotrimeric VHH binds to BoNT with a Limit of Quantification (LOQ) of at least about 25 aM. In some embodiments, the heterotrimer carries a decalysine (K10) stretch of amino acids at its N-terminus for better binding onto an amino reactive solid support matrix.

Tags, Linkers, and Spacers

In certain aspects, the VHH (including multimeric VHHs, such as heterotrimers, dimers, trimers, tetramers, etc.) is modified, for example, by incorporation of or attachment (directly or indirectly (e.g., via a linker)) of one or more tags. A tag is a molecule (e.g. antibody epitope) that is attached or genetically fused to the VHH (such as, multimeric VHHs) and to which the anti-tag antibody binds. Genetic fusion refers to a recombinant protein that is engineered to contain extra amino acid sequences that constitute the tag. Thus, the DNA encoding the tag is joined (in reading frame) with the DNA encoding the binding agent.

The tag can be attached to a portion of the VHH (such as, a multimeric VHH) so long as the tag does not interfere with the VHH's ability to bind to a disease agent, such as BoNT. The tag, for example, can be a polypeptide, sugar, or DNA molecule.

In certain embodiments, the tag is incorporated by genetic fusion at the carboxyl end of the VHH (such as, a multimeric VHH). The tag, itself, can also be a polypeptide joined at the amino terminal end or within the VHH (such as between VHH domains of a multimeric VHH) as long as the tag does not affect binding of the binding agent to the target and the tag remains accessible to the anti-tag mAb. In embodiments, the tag itself does not interact or bind with the disease agent. Preferably, the tag is an uncommon or unique molecule or peptide in nature. In an aspect, the tag is a polyptepide that ranges from about 5 amino acids to about 20 amino acids, and preferably between about 8 and about 15 amino acids in length. In embodiments, the tag is a polypeptide that is about 5 amino acids in length. In embodiments, the tag is a polypeptide that is about 6 amino acids in length. In embodiments, the tag is a polypeptide that is about 7 amino acids in length. In embodiments, the tag is a polypeptide that is about 8 amino acids in length. In embodiments, the tag is a polypeptide that is about 9 amino acids in length. In embodiments, the tag is a polypeptide that is about 10 amino acids in length. In embodiments, the tag is a polypeptide that is about 11 amino acids in length. In embodiments, the tag is a polypeptide that is about 12 amino acids in length. In embodiments, the tag is a polypeptide that is about 13 amino acids in length. In embodiments, the tag is a polypeptide that is about 14 amino acids in length. In embodiments, the tag is a polypeptide that is about 15 amino acids in length. In embodiments, the tag is a polypeptide that is about 16 amino acids in length. In embodiments, the tag is a polypeptide that is about 17 amino acids in length. In embodiments, the tag is a polypeptide that is about 18 amino acids in length. In embodiments, the tag is a polypeptide that is about 19 amino acids in length. In embodiments, the tag is a polypeptide that is about 20 amino acids in length. In embodiments, the tag is a polypeptide that is about 21 amino acids in length. In embodiments, the tag is a polypeptide that is about 22 amino acids in length. In embodiments, the tag is a polypeptide that is about 23 amino acids in length. In embodiments, the tag is a polypeptide that is about 24 amino acids in length. In embodiments, the tag is a polypeptide that is about 25 or more amino acids in length. Non-limiting examples of such tags also include c-myc and haemagglutinin protein, biotin, avidin, hapten (e.g., a carbohydrate or nucleotide), thioredoxin (Trx), an E-tag (i.e. a GAPVPYPDPLEPR peptide recognized by an antibody), an S-tag (i.e. a KETAAAKFERQHMDS peptide recognized by an antibody), and the like.

The tag can be incorporated into the binding agent using recombinant technology in which the DNA encodes the VHH (such as, a multimeric VHH) genetically fused with the tag. Specifically, the coding sequence for the tag can be cloned into an expression vector and transfected into cells for recombinant expression. Once the tag is incorporated into the binding agent, the VHH (such as, a multimeric VHH), like an antibody, can be evaluated for its ability and affinity to bind to BoNT.

Inclusion of more than one copy of the tag on a VHH, in certain aspects, has additional advantages, such as by increasing the number of anti-tag antibodies that can bind to the binding agent. One or more tags can be attached to the binding agent. In the case of multimeric VHHs (such as a heterotrimeric VHH), they can have one tag, a single tag per monomer, or any number of tags (e.g., 1, 2, 3, 4, 5, 6, 7, 8, 9, 10, or more tags). In some embodiments, the VHH carries a tag (for example, a decalysine (K10) stretch of amino acids) at its N-terminus or C-terminus oriented in such a way as to improve or to facilitate binding onto a solid support (such as an amino reactive solid support matrix or to a reactive surface on a bead).

Optionally, a linker or spacer can be used to attach the binding region of the VHH (such as, a multimeric VHH) with the tag. A linker can be used to indirectly attach a tag to the binding region. In one embodiment of the invention, the VHH (such as, a multimeric VHH) includes one or more binding region(s), linker(s) and/or tag(s).

In embodiments, any of the multimeric VHHs disclosed herein (such as heterotrimeric VHHs) can have one or more N-terminally located tags, such as a decalysine tag, a Trx tag, and/or an S-tag. These tags can be located either N-terminally or C-terminally to the most N-terminal VHH domain (such as an H7* domain) of the multimeric VHH. In embodiments, one or more tags can be located in between one or more VHH domains of a multimeric VHH (for example, an E-tag can be located in between the N-terminal VHH domain and the central VHH domain in a trimeric VHH). In other embodiments, any of the tags disclosed herein can be located at the C-terminal end of a multimeric VHH (for example, an E-tag can be located C-terminally to the most C-terminal VHH domain in a trimeric VHH).

With respect to multimeric VHHs, linkers may be used to separate individual VHH domains. These linkers can be a polypeptide having a sequence that ranges from about 5 to about 300 amino acids in length. In embodiments, the linker is about 25-275, In embodiments, the linker is about 50-250 amino acids in length. In embodiments, the linker is about 75-225 amino acids in length. In embodiments, the linker is about 100-200 amino acids in length. In embodiments, the linker is about 125-175 amino acids in length. In embodiments, the linker is about 25-100 amino acids in length. In embodiments, the linker is about 50-150 amino acids in length. In embodiments, the linker is about 150-250 amino acids in length. In embodiments, the linker is a polypeptide having a sequence any of about 5 amino acids in length. In embodiments, the linker is a polypeptide having a sequence any of about 10 amino acids in length. In embodiments, the linker is a polypeptide having a sequence any of about 15 amino acids in length. In embodiments, the linker is a polypeptide having a sequence any of about 20 amino acids in length. In embodiments, the linker is a polypeptide having a sequence any of about 25 amino acids in length. In embodiments, the linker is a polypeptide having a sequence any of about 30 amino acids in length. In embodiments, the linker is a polypeptide having a sequence any of about 35 amino acids in length. In embodiments, the linker is a polypeptide having a sequence any of about 40 amino acids in length. In embodiments, the linker is a polypeptide having a sequence any of about 45 amino acids in length. In embodiments, the linker is a polypeptide having a sequence any of about 50 amino acids in length. In embodiments, the linker is a polypeptide having a sequence any of about 55 amino acids in length. In embodiments, the linker is a polypeptide having a sequence any of about 60 amino acids in length. In embodiments, the linker is a polypeptide having a sequence any of about 65 amino acids in length. In embodiments, the linker is a polypeptide having a sequence any of about 70 amino acids in length. In embodiments, the linker is a polypeptide having a sequence any of about 75 amino acids in length. In embodiments, the linker is a polypeptide having a sequence any of about 80 amino acids in length. In embodiments, the linker is a polypeptide having a sequence any of about 85 amino acids in length. In embodiments, the linker is a polypeptide having a sequence any of about 90 amino acids in length. In embodiments, the linker is a polypeptide having a sequence any of about 95 amino acids in length. In embodiments, the linker is a polypeptide having a sequence any of about 100 amino acids in length. In embodiments, the linker is a polypeptide having a sequence any of about 105 amino acids in length. In embodiments, the linker is a polypeptide having a sequence any of about 110 amino acids in length. In embodiments, the linker is a polypeptide having a sequence any of about 115 amino acids in length. In embodiments, the linker is a polypeptide having a sequence any of about 120 amino acids in length. In embodiments, the linker is a polypeptide having a sequence any of about 125 amino acids in length. In embodiments, the linker is a polypeptide having a sequence any of about 130 amino acids in length. In embodiments, the linker is a polypeptide having a sequence any of about 135 amino acids in length. In embodiments, the linker is a polypeptide having a sequence any of about 140 amino acids in length. In embodiments, the linker is a polypeptide having a sequence any of about 145 amino acids in length. In embodiments, the linker is a polypeptide having a sequence any of about 150 amino acids in length. In embodiments, the linker is a polypeptide having a sequence any of about 155 amino acids in length. In embodiments, the linker is a polypeptide having a sequence any of about 160 amino acids in length. In embodiments, the linker is a polypeptide having a sequence any of about 165 amino acids in length. In embodiments, the linker is a polypeptide having a sequence any of about 170 amino acids in length. In embodiments, the linker is a polypeptide having a sequence any of about 175 amino acids in length. In embodiments, the linker is a polypeptide having a sequence any of about 180 amino acids in length. In embodiments, the linker is a polypeptide having a sequence any of about 185 amino acids in length. In embodiments, the linker is a polypeptide having a sequence any of about 190 amino acids in length. In embodiments, the linker is a polypeptide having a sequence any of about 195 amino acids in length. In embodiments, the linker is a polypeptide having a sequence any of about 200 amino acids in length. In embodiments, the linker is a polypeptide having a sequence any of about 205 amino acids in length. In embodiments, the linker is a polypeptide having a sequence any of about 210 amino acids in length. In embodiments, the linker is a polypeptide having a sequence any of about 215 amino acids in length. In embodiments, the linker is a polypeptide having a sequence any of about 220 amino acids in length. In embodiments, the linker is a polypeptide having a sequence any of about 225 amino acids in length. In embodiments, the linker is a polypeptide having a sequence any of about 230 amino acids in length. In embodiments, the linker is a polypeptide having a sequence any of about 235 amino acids in length. In embodiments, the linker is a polypeptide having a sequence any of about 240 amino acids in length. In embodiments, the linker is a polypeptide having a sequence any of about 245 amino acids in length. In embodiments, the linker is a polypeptide having a sequence any of about 250 amino acids in length. In embodiments, the linker is a polypeptide having a sequence any of about 255 amino acids in length. In embodiments, the linker is a polypeptide having a sequence any of about 260 amino acids in length. In embodiments, the linker is a polypeptide having a sequence any of about 265 amino acids in length. In embodiments, the linker is a polypeptide having a sequence any of about 270 amino acids in length. In embodiments, the linker is a polypeptide having a sequence any of about 275 amino acids in length. In embodiments, the linker is a polypeptide having a sequence any of about 280 amino acids in length. In embodiments, the linker is a polypeptide having a sequence any of about 285 amino acids in length. In embodiments, the linker is a polypeptide having a sequence any of about 290, In embodiments, the linker is a polypeptide having a sequence any of about 295 amino acids in length. In embodiments, the linker is a polypeptide having a sequence any of about or 300 or more amino acids in length.

In other embodiments, the linker can be any compound, now known or later developed, that can attach the binding region with a tag or join two VHH domains in the case of multimeric (such as heterotrimeric) VHHs. Multimeric VHHs can have any of 1, 2, or three or more linkers separating the individual VHH domains in the multimer. For example, a trimeric VHH can have one or two linker sequences and the linker sequence(s) can be located either (1) between the N-terminal VHH domain and the central VHH domain, (2) between the central VHH domain and the C-terminal VHH domain, or (3) between both the N-terminal VHH domain and the central VHH domain and the central VHH domain and the C-terminal VHH domain. In embodiments, the linker can include one or more (such as 1, 2, 3, 4, or 5) ER/K α-helices (Sivaramakrishnan and Spudich, 2011 *Proc Natl Acad Sci USA*. 2011 Dec. 20; 108(51): 20467-72, the disclosure of which is incorporated by reference herein). The ER/K α-helix linker can vary in length, such as any of about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, or 50 nm, or more in length. In embodiments, the ER/K α-helix linker is 10 nm in length and comprises the amino acid sequence EEEEKKKQQEEE-AERLRRIQEEMEKERKRREEDEERRRKEEEERRMK-LEMEAKRKQ EEEERKKREDDEKRKKK (SEQ ID NO:12). In other embodiments, the ER/K α-helix linker is 30 nm in length and comprises the amino acid sequence EEEEKKKEEEEKKQKEEQERLAKEEAERKQKEEQE-RLAKEEAERKQKEEEERKQKE EEERKQKEEEERKL-KEEQERKAAEEKKAKEEAERKAKEEQERKAEEERK-KKEEEER LERERKEREEQEKKAKEEAERIAKLEAEK-KAEEERKAKEEEERKAKEEEERKKKEEQ ERLAKE-KEEAERKAAEEKKAKEEQERKEKEEAERKQR (SEQ ID NO:13). In other embodiments, the linker can be either a serine-rich linker or a glycine rich linker. As used herein, "serine-rich" linker and "glycine-rich" linker refer to a linker that contains about 50% to about 100% serine or glycine residues, respectively. A "serine-glycine-rich liner" contains about 50% to about 100% serine and glycine residues. In embodiments, the linker contains any of about 50%, 60%, 70%, 80%, 90%, or 100% serine and/or lysine residues, respectively (or combinations of the same), inclusive of values falling in between these percentages. In other embodiments, the linker contains about 50% serine and/or lysine residues. In other embodiments, the linker contains about 70% serine and/or lysine residues. In other embodiments, the linker contains about 60% serine and/or lysine residues. In other embodiments, the linker contains about 80% serine and/or lysine residues. In other embodiments, the linker contains about 90% serine and/or lysine residues. In other embodiments, the linker contains about 100% serine and/or lysine residues.

Nucleic Acids

The present invention also encompasses isolated nucleic acid sequences that encode the VHHs disclosed herein and in particular, those which encode a polypeptide molecule having an amino acid sequence of SEQ ID NOs: 1, 2, or 3. As used herein, an "isolated nucleotide sequence" is a sequence that is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences of the binding agents of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the VHH binding agents described herein. In particular, the present invention is directed to nucleic acid molecules having at least about 70% (e.g., 75%, 80%, 85%, 90% or 95%) identity with SEQ ID NO: 4. Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleic acid need not reflect the exact sequence of the sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown. et al., Nature, 366:575 (1993); and further defined in conjunction with certain assays.

Vectors and Host Cells

The invention also provides vectors, plasmids or viruses containing one or more of the nucleic acid molecules having the sequence of SEQ ID NO:4 or the sequence of the nucleic acid molecules encoding the amino acids of SEQ ID NOs: 1, 2, or 3. Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology. (Current Protocol, 1994) and Sambrook et al., "Molecular Cloning: A Laboratory Manual," 2nd ED. (1989).

Any of a variety of expression vectors known to those of ordinary skill in the art can be employed to express the VHHs of this invention. Expression can be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner can encode any of the polypeptides described herein including variants thereof.

Methods of Use

Methods for Detecting Botulinum Neurotoxin

The Assay with a Large Immuno-sorbent Surface Area (ALISSA) requires affinity capture of BoNT from a biological sample onto a solid support matrix such as beads or a column. Subsequently, the intrinsic zinc metalloprotease activity of immobilized BoNT is measured using a fluorogenic or bioluminogenic substrate. The ALISSA requires an affinity reagent, such as an antibody, to capture BoNT without inactivating its enzymatic activity. The current disclosure describes the use of a BoNT affinity reagent based on alpaca single chain antibody binding domains (VHHs) for detecting BoNT in a sample.

In certain embodiments, the ALISSA is employed for the detection of botulinum toxin (BoNT). In other embodiments, the ALISSA is employed for the detection of botulinum toxin A (BoNT/A). In certain embodiments, the turnaround time for the ALISSA is one to two hours, which is significantly faster than other BoNT detection assays such as the life mouse assay (~48 hours) as well as ELISA (~3 hours). The exemplary experimental results obtained herein were obtained with BoNT type A (BoNT/A), but could be applied just as easily to other BoNT scrotypes or other toxins as well as to enzymes.

The ALISSA avoids interference with other sample components by using a highly specific affinity matrix and exploiting the natural catalytic activity of the toxin or enzyme ("target") with a target-specific substrate. Both of these steps amplify the signal via localized enrichment of the toxin and enzymatic conversion of multiple substrate molecules per toxin molecule.

In certain embodiments, ALISSA consists of two main steps: 1) capture and enrichment of toxin or enzyme on a bead-based immuno-affinity matrix and removal of unspecific binding molecules, and 2) determination/detection of the enzymatic activity of the immobilized toxin or enzyme based on cleavage of a specific fluorigenic or bioluminescent substrate. In certain embodiments, the immuno-affinity matrix consists of protein-A conjugated sepharose beads coupled and cross-linked to anti-toxin or anti-enzyme VHHs (such as single domain VHHs or multimeric VHHs, e.g. heterotrimeric VHHs, such as any of those disclosed herein). For example, the immunoaffinity matrix can consist of protein-A conjugated sepharose beads coupled and cross-linked to anti-BoNT VHHs. The immunosorbent support provided herein can be comprised of either loose beads or one or more fixed column.

In accordance with the method of the invention, one or more sample from a source suspected of containing a toxin is obtained and then contacted with a substrate composition comprising a toxin substrate, such as a fluorogenic or luminogenic substrate or a mixture thereof, for a period of time and under conditions sufficient to permit the toxin to react with the toxin substrate to cause a measurable change in a property such as fluorescence or light emission, or the resulting reaction product.

In general, the toxin or enzyme contained in the sample is first captured on an enrichment matrix such as a bead-based immuno-affinity matrix containing immobilized anti-toxin specific VHHs (such as single domain VHHs or multimeric VHHs, e.g. heterotrimeric VHHs, such as any of those disclosed herein). Immobilization of the VHHs to the matrix can be by a variety of methods, including, for example by covalent crosslinking the VHH to the beads. Once captured, the toxin or enzyme molecules retain enzymatic function and specificity for its substrate.

The natural substrate of BoNT/A is the 25-kDa synaptosomal-associated protein (SNAP 25), which it cleaves at distinct sites, thereby preventing the release of neurotransmitters (Schiavo 1993a; Schiavo 1993b). In those embodiments wherein BoNT/A is being detected, the enzymatic activity of BoNT/A may be utilized to cleave the fluorigenic substrate SNAPtide, which is a synthetic, commercially available, 13-amino acid peptide that contains the native SNAP-25 cleavage site for BoNT/A (U.S. Pat. No. 6,504,006, incorporated by reference herein). In those embodiments wherein a BoNT type other than type A is being detected, the fluorogenic substrate may be any substrate that is specifically cleaved by the BoNT type being detected. In those embodiments were a different class or type of toxin other than a BoNT is being detected, the substrate may be any substrate that is specifically cleaved or catalyzed by the toxin being detected.

The present invention provides a method for detecting toxin or enzyme which avoids interference with other sample components by use of high toxin-specific affinity matrix and toxin-specific substrates. For example, use of a high affinity BoNT/A specific matrix and a BoNT/A-specific substrate reduces or avoids interference by other components present within a sample thus amplifying the signal and increasing the assay's sensitivity. Use of a toxin-specific substrate also exploits the natural proteolytic activity of the toxin. Signal amplification is achieved by localized enrichment of the toxin and through enzymatic conversion of substrate molecules. In certain embodiments, the capture matrix is designed to stably enrich the toxin while retaining enzymatic activity. The capture matrix may also purify toxin from non-specific components or proteases present within the sample. Use of a beaded protein A matrix to bind anti-toxin VHHs allows orientation of the VHH away from the bead surface and into the surrounding fluid. This augments and provides increased accessibility for toxin molecules. Use of a bead-based assays also allows for wash steps that diminish interference by other proteases. The present invention provides a considerably faster and more sensitive method for detecting toxin and its activity.

In some embodiments, detection of BoNT serotypes including subtypes is also achieved utilizing fluorogenic or luminogenic substrates. The botulinum neurotoxins cleave a variety of vertebral SNARE (Soluble NSF attachment protein receptor) in vivo and in vitro. While some fluorogenic BoNT substrates based on natural SNARE sequence are known (Schmidt 2003), the possible interference by sterically demanding fluorophore or quencher moieties on the catalytic cleavage reaction of such fluorogenic peptides remains a concern. The present invention provides novel substrates that achieve higher chemical stability and comparable or superior sensitivity as compared to prior peptides. Preferably, fluorophore substrates that allow for efficient cleavable fluorophore and quencher combinations are selected for use in the ALISSA. Generally, fluorophore and quencher require proximities of about 10 nm or less to allow sufficient FRET-mediated quenching. Closer distances are also preferred to reduce background fluorescence from the quenched substrates. In certain embodiments, use of bioluminescent substrates to allow for luminescent BoNT detection may be desired. Luminescent based assays can reduce or omit the requirement for a light source and provide greater signal-to-noise ratios. Bioluminescent light in particular, can be detected using less complex means such as with miniaturized photomultipliers or microscopic avalanche photodiodes. Furthermore, potential interference from background fluorescence due to inert components of a microfluidic device are alleviated.

Fluorogenic substrates for BoNT serotypes such as serotypes A to G are designed through use of peptide libraries having proteinogenic and as well as non-proteinogenic amino acids. Preferably, those substrates having resistance to non-BoNT proteases are selected for use with the ALISSA or other immobilized antibody or VHH matrix-based assay. More preferably, substrates designed so as to be more specifically and readily cleaved by BoNT are also provided. Thus, the present invention includes methods for detecting BoNT of all serotypes and subtypes in one or more biological sample, in vitro or in vivo using affinity capture of BoNT on microscopic beads coated with antibodies specific to the toxin. The antibody captured toxin retains its metalloprotease activity. The method includes use of a reporter molecule such as a fluorogenic or bioluminescent substrate that is cleavable by one or more molecules of the captured BoNT. Fluorescence is then detected using a handheld ultraviolet (UV) light, a fluorescence excitation and/or detecting tool, device or any suitable commercially available fluorometer. Luminescence is detected using any suitable commercially available luminometer.

In embodiments, provided herein are inexpensive, robust method providing high analytical specificity and attomolar (aM) sensitivity for detection of toxin or enzyme in complex biological samples. The methods may improve the diagnosis of botulism and other toxins significantly and protect humans in biomedical and bio-defense scenarios. The method may also be applied for the routine testing of foods and for forensic investigation.

Accordingly, in a first aspect, there is provided a method for detecting the presence of a botulinum toxin in a sample. The method includes a) exposing the sample containing a botulinum toxin to (i) an anti-botulinum neurotoxin camelid-derived single chain antibody binding domain (VHH) and (ii) a detectable toxin substrate, thereby forming a detectable toxin substrate-VHH complex. The method further includes b) detecting the detectable toxin substrate-VHH complex. In some embodiments, the camelid-derived VHH is derived from a species selected from the group consisting of camels, llamas, alpacas, vicuñas, and guanacos. In other embodiments, the camelid-derived VHH is derived from an alpaca. In yet other embodiments, the alpaca is a Huacaya Alpaca or a Suri alpaca.

Methods of Treatment

The present invention also includes methods of administering a therapeutically effective amount of a binding agent comprising one or more anti-botulinum neurotoxin camelid-derived single chain antibody binding domains (VHHs), including multimeric (e.g., heterotrimeric) VHHs, as described herein, to an individual. As used herein, "therapeutically effective amount" refers to an amount which is effective in reducing, eliminating, treating, preventing or controlling the symptoms of a disease or condition (such as, botulism). The term "controlling" is intended to refer to all processes wherein there may be a slowing, interrupting, arresting, or stopping of the progression of a diseases and condition, but does not necessarily indicate a total elimination of all disease and condition symptoms, and is intended to include prophylactic treatment.

The binding agent can be administered as a monomer, or as a multimeric binding construct comprising more than one monomer (such as, without limitation, a dimer, a trimer, a tetramer, or other multimer). The methods involve administration of one or more binding agents that include monomers that each has a binding region that is specific to a disease agent (such as a botulinum neurotoxin). In embodiments, any of the following combinations of binding agents can be administered: a single monomer, multiple (e.g., two or more) monomers, a multimeric binding agent comprising more than one monomer, multiple (e.g., two or more) multimeric binding agents comprising more than one monomer, or any combination thereof. In some embodiments, the binding agent is a part of a pharmaceutical composition additionally comprising one or more additional elements including, for example, carriers or pharmaceutically acceptable excipients, as described herein.

Administration of one or more binding agent can occur simultaneously or sequentially in time. The binding agents can be administered before, after or at the same time as another binding agent, so long as they are administered close enough in time to have the desired effect (e.g., before the binding agents have been cleared by the body). Thus, the term "co-administration" is used herein to mean that the binding agents and another binding agent will be administered at times to achieve treatment of the disease, or reduction in the level of the pathogen (e.g., a botulinum neurotoxin) and/or symptoms associated with it. The methods of the present invention are not limited to the sequence in which the binding agents are administered; so long as the compositions are administered close enough in time to produce the desired effect. In embodiments, the binding agents can also be co-administered with other medications or compositions normally administered when treating botulinum neurotoxin.

Administration of the binding agent ameliorates or reduces the severity of one or more the symptoms of the disease or condition (such as, botulism). The presence, absence or severity of symptoms can be measured using tests and diagnostic procedures known in the art. Similarly the presence, absence and/or level of the disease agent can be measured using methods known in the art. Symptoms or levels of the disease agent can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the disease agent, or severity of symptoms indicates that treatment is not working. Symptoms and levels of disease agents are measured using methods known in the art.

The binding agent comprising one or more anti-botulinum neurotoxin camelid-derived single chain antibody binding domains (VHHs) disclosed herein can be administered in one or more pharmaceutical carriers. The terms "pharmaceutically acceptable carrier" or a "carrier" refer to any generally acceptable excipient or drug delivery device that is relatively inert and non-toxic. The binding agents can be administered with or without a carrier. Exemplary carriers include calcium carbonate, sucrose, dextrose, mannose, albumin. starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The binding agents ibody can be administered systemically or locally (e.g., by injection or diffusion).

Suitable carriers (e.g., pharmaceutical carriers) also include, but are not limited to sterile water, salt solutions (such as Ringer's solution or saline (e.g. isotonic saline)), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances. e.g., enzyme inhibitors, to reduce metabolic degradation. A carrier (e.g., a pharmaceutically acceptable carrier) is preferred, but not necessary to administer one or more binding agents disclosed herein.

The binding agents of the present invention can be administered intravenously, parenterally, orally, nasally, by inhalation, by implant, by injection, or by suppository. The composition can be administered in a single dose or in more than one dose over a period of time to confer the desired effect.

The actual effective amounts of compositions of the present invention can vary according to the binding agent being utilized, the particular composition formulated, the mode of administration and the age, weight and condition of the patient, for example. As used herein, an effective amount of the binding agents is an amount which is capable of reducing one or more symptoms of the disease or conditions caused by the disease agent (such as, botulinum neurotoxin). Dosages for a particular patient can be determined by one of ordinary skill in the art using conventional considerations, (e.g. by means of an appropriate, conventional pharmacological protocol).

Systems or Kits

Systems or kits of the present invention include one or more VHHs and, optionally, one or more tags and an anti-tag antibody having an anti-tag region as described herein. In other embodiments, systems or kits of the present invention further include an enrichment matrix such as a bead-based immuno-affinity matrix containing immobilized anti-toxin specific VHHs (such as single domain VHHs or multimeric VHHs, e.g. heterotrimeric VHHs, such as any of those disclosed herein). In other embodiments, systems or kits of the present invention further include a detectable toxin substrate, such as a fluorogenic or luminogenic substrate. In some embodiments, the fluorogenic or luminogenic substrate comprises one or more of Lys[5-Fam]IleAspGluAlaAsnGlnArgAlaThrLys[DABCYL]X, wherein X is norleucine; 5-Fam-Lys[5-Fam]IleAspGluAlaAsnGlnArgAlaThrLys[DABCYL]X, wherein X is norleucine; or 5-Fam-LysIleAspGluAlaAsnGlnArgAlaThrLys[DABCYL]Nle.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition. Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons. Inc., New York, 2000, (including supplements through 2014) and *Gene Transfer and Expression in Mammalian Cells* (Makrides, ed., Elsevier Sciences B.V., Amsterdam, 2003).

Example 1

Two BoNT specific VHHs that were previously disclosed were used in the currently disclosed studies. These are referred to as H7 and C2. H7 binds the light chain of BoNT serotype A while C2 binds its heavy chain. Using the yeast display method of Witrup (*Nature Protocols* (2006), 1(2), 755-768), we have affinity matured the H7 VHH, which enhanced its affinity from 42 pM to 12 pM. The matured H7 (named H7*) has four mutations compared to the original as shown in FIG. 1.

Example 2

We have generated several concatenated VHH fusion proteins and optimized the amino acid spacers between the VHHs through trial and error, by screening suitable compounds in the ALISSSA. Consequentially, we generated a heterotrimeric VHH that contains two H7* and one C2 VHH (H7*-H7*-C2). This heterotrimer was generated as a synthetic gene with optimized codons and secondary RNA structure for bacterial expression in *E. coli*. In addition the heterotrimer carries a decalysine (K10) stretch of amino acids at its N-terminus for better binding onto an amino reactive solid support matrix. When the H7*-H7*-C2 heterotrimer was tested in the BoNT/A ALISSA, we achieved a Limit of Quantification (LOQ) of 25 attomolar (aM) for the BoNT/A holotoxin, as set forth in FIG. 2.

Example 3

The H7*-H7*-C2 hetrotrimer is encoded within a pET28 vector, having the feature map disclosed in FIG. 3 and sequence disclosed in FIG. 4.

REFERENCES

Ammon, S. S. et al. Botulinum toxin as a biological weapon: medical and public health management. Jama 285, 1059-1070 (2001); Wein, L. M. & Liu, Y. Analyzing a bioterror attack on the food supply: the case of botulinum toxin in milk. Proc Natl Acad Sci USA 102, 9984-9989 (2005); Arnon, S. S., Schechter, R., Maslanka, S. E., Jewell, N. P. & Hatheway, C. L. Human botulism immune globulin for the treatment of infant botulism. N Engl J Med 354, 462-471 (2006); Schantz, E. J. & Johnson, E. A. Properties and use of botulinum toxin and other microbial neurotoxins in medicine. Microbiol. Rev 56, 80-99 (1992); Sakaguchi, G. *Clostridium botulinum* toxins. Pharmacol Ther 19, 165-194 (1982); Chen, F., Kuziemko, G. M. & Stevens, R. C. Biophysical characterization of the stability of the 150-kilodalton botulinum toxin, the nontoxic component, and the 900-kilodalton botulinum toxin complex species. Infect Immun 66, 2420-2425 (1998); Sharma, S. K., Ramzan, M. A. & Singh, B. R. Separation of the components of type A botulinum neurotoxin complex by electrophoresis. Toxicon 41, 321-331 (2003); Melling, J., Hambleton, P. & Shone, C. C. *Clostridium botulinum* toxins: nature and preparation for clinical use. Eye 2 (Pt 1), 16-23 (1988); Zhang, L., Lin, W. J., Li, S. & Aoki, K. R. Complete DNA sequences of the botulinum neurotoxin complex of *Clostridium botulinum* type A-Hall (Allergan) strain. Gene 315, 21-32 (2003); Aoki, K. R. & Guyer, B. Botulinum toxin type A and other botulinum toxin serotypes: a comparative review of biochemical and pharmacological actions. Eur J Neurol 8 Suppl 5, 21-29 (2001); Smith, L. D. The occurrence of *Clostridium botulinum* and *Clostridium tetani* in the soil of the United States. Health Lab Sci 15, 74-80 (1978); Schiavo, G., Matteoli, M. & Montecucco, C. Neurotoxins affecting neuroexocytosis. Physiol Rev 80, 717-766 (2000); Kurazono, H. et al. Minimal essential domains specifying toxicity of the light chains of tetanus toxin and botulinum neurotoxin type A. J Biol Chem 267, 14721-14729 (1992); Lacy, D. B., Tepp, W., Cohen, A. C., DasGupta, B. R. & Stevens, R. C. Crystal structure of botulinum neurotoxin type A and implications for toxicity. Nat Struct Biol 5, 898-902 (1998); Cai, S., Sarkar, H. K. & Singh, B. R. Enhancement of the endopeptidase activity of botulinum neurotoxin by its associated proteins and dithiothreitol. Biochemistry 38, 6903-6910 (1999); Cai, S. & Singh, B. R. Role of the disulfide cleavage induced molten globule state of type a botulinum neurotoxin in its endopeptidase activity. Biochemistry 40, 15327-15333 (2001); Ferreira, J. L., Maslanka, S., Johnson, E. & Goodnough, M. Detection of botulinal neurotoxins A, B, E, and F by amplified enzyme-linked immunosorbent assay: collaborative study. J AOAC Int 86, 314-331 (2003); Kautter, D. A. & Solomon, H. M. Collaborative study of a method for the detection of *Clostridium botulinum* and its toxins in foods. J Assoc Off Anal Chem 60, 541-545 (1977); Sharma, S. K., Ferreira, J. L., Eblen, B. S. & Whiting, R. C. Detection of type A, B, E, and F *Clostridium botulinum* neurotoxins in foods by using an amplified enzyme-linked immunosorbent assay with digoxigenin-labeled antibodies. Appl Environ Microbiol 72, 1231-1238 (2006); Sugiyama, H. *Clostridium botulinum* neurotoxin. Microbiol. Rev 44, 419-448 (1980); Varnum, S. M. et al. Enzyme-amplified protein microarray and a fluidic renewable surface fluorescence immunoassay for botulinum neurotoxin detection using high-affinity recombinant antibodies. Analytica Chimica Acta 570, 137-143 (2006); Kalb, S. R. et al. The use of Endopep-MS for the detection of botulinum toxins A, B, E, and F in serum and stool samples. Anal Biochem 351, 84-92 (2006); Barr, J. R. et al. Botulinum neurotoxin detection and differentiation by mass spectrometry. Emerg Infect Dis 11, 1578-1583 (2005); Kalb, S. R., Goodnough, M. C., Malizio, C. J., Pirkle, J. L. & Barr, J. R. Detection of botulinum neurotoxin A in a spiked milk sample with subtype identification through toxin proteomics. Anal Chem 77, 6140-6146 (2005); Boyer, A. E. et al. From the mouse to the mass spectrometer: detection and differentiation of the endoproteinase activities of botulinum neurotoxins A-G by mass spectrometry. Anal Chem 77, 3916-3924 (2005); Chao, H. Y., Wang, Y. C., Tang, S. S. & Liu, H. W. A highly sensitive immuno-polymerase chain reaction assay for *Clostridium botulinum* neurotoxin type A. Toxicon 43, 27-34 (2004); Mason, J. T., Xu, L., Sheng, Z. M. & O'Leary, T. J. A liposome-PCR assay for the ultrasensitive detection of biological toxins. Nat Biotechnol 24, 555-557 (2006); Mason, J. T., Xu, L., Sheng, Z. M., He, J. & O'Leary, T. J. Liposome polymerase chain reaction assay for the sub-attomolar detection of cholera toxin and botulinum neurotoxin type A. Nature Protocols 1, 2003-2011 (2006); Ekong, T. A., McLellan, K. & Sesardic, D. Immunological detection of *Clostridium botulinum* toxin type A in therapeutic preparations. J Immunol Methods 180, 181-191 (1995); Schmidt, J. J. & Stafford, R. G. Fluorigenic substrates for the protease activities of botulinum neurotoxins, serotypes A, B, and F. Appl Environ Microbiol 69, 297-303 (2003); Schiavo, G. et al. Identification of the nerve terminal targets of botulinum neurotoxin serotypes A, D, and E. J Biol Chem 268, 23784-23787 (1993); Schiavo, G. et al. Botulinum neurotoxins serotypes A and E cleave SNAP-25 at distinct COOH-terminal peptide bonds. FEBS Lett 335, 99-103 (1993).

The invention claimed is:

1. A single chain antibody binding domain (VHH) comprising (a) a first complementary determining region amino acid sequence (CDR1) comprising GSGISGIA (SEQ ID NO:5), (b) a second complementary determining region amino acid sequence (CDR2) comprising IFSGGST (SEQ ID NO:6) and (c) a third complementary determining region amino acid sequence (CDR3) comprising RLYGSGDYWVQ (SEQ ID NO:7), wherein the VHH binds to botulinum neurotoxin with a dissociation constant (Kd) of less than 40 pM.

2. The VHH of claim 1, further comprising a framework (FW) region amino acid sequence comprising (a) QVQLVESGGGLVQVGGSLRLSCVVS (SEQ ID NO:8); (b) MGWYRQAPGKRREMVAD (SEQ ID NO:9); (c) GSVKGRFTISRDNAKKTSYLQMNN AKPEDTGAYYC (SEQ ID NO:10); or (d) GTQVTVSSAHHSED (SEQ ID NO:11).

3. The VHH of claim 1, further comprising a framework (FW) region amino acid sequence comprising (a) QVQLVESGGGLVQVGGSLRLSCVVS (SEQ ID NO:8); (b) MGWYRQAPGKRREMVAD (SEQ ID NO:9); (c) GSVKGRFTISRDNAKKTSYLQMNN AKPEDTGAYYC (SEQ ID NO:10); and (d) GTQVTVSSAHHSED (SEQ ID NO:11).

4. The VHH of claim 1, comprising the amino acid sequence QVQLVESGGGLVQVGGSLRLSCVVSGSGISGIAMGWYRQAPGKRREMVADIFSGGSTDYA GSVKGRFTISRDNAKKTSYLQMNNAKPEDTGAYYCRLYGSGDYWVQGTQVTVSSAHHSE D (SEQ ID NO:3).

5. The VHH of claim 1, wherein the VHH binds to botulinum neurotoxin with a Kd of at least 12 pM.

6. The VHH of claim 5, wherein said toxin is botulinum neurotoxin serotype A (BoNT/A).

7. A nucleic acid encoding the VHH of claim 1.

8. A vector comprising the nucleic acid of claim 7.

9. A cell comprising the vector of claim 8.

10. A multimeric single chain antibody binding domain (VHH) construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKSGIV (SEQ ID NO:15) and CDR3 NVGEF (SEQ ID NO:16), wherein at least one of the first VHH or the second VHH are the VHH of claim 1.

11. A nucleic acid encoding the multimeric VHH construct of claim 10.

12. A vector comprising the nucleic acid of claim 11.

13. A cell comprising the vector of claim 12.

14. A method for detecting the presence of a botulinum neurotoxin in a sample comprising:
a) contacting a botulinum neurotoxin with (i) the single chain antibody binding domain (VHH) of claim 1 or (ii) a multimeric VHH construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKSGIV (SEQ ID NO:15) and CDR3 NVGEF (SEQ ID NO:16) and wherein at least one of the first VHH or the second VHH are the VHH of claim 1, thereby forming a VHH-botulinum neurotoxin complex; and
b) detecting the VHH-botulinum neurotoxin complex.

15. A kit comprising:
a) (i) the single chain antibody binding domain (VHH) of claim 1 or (ii) a multimeric VHH construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKSGIV (SEQ ID NO:15) and CDR3 NVGEF (SEQ ID NO:16) and wherein at least one of the first VHH or the second VHH are the VHH of claim 1; and
b) a detectable toxin substrate.

16. A pharmaceutical composition comprising (a)(i) the single chain antibody binding domain (VHH) of claim 1 or (ii) a multimeric VHH construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKSGIV (SEQ ID NO:15) and CDR3 NVGEF (SEQ ID NO:16) and wherein at least one of the first VHH or the second VHH are the VHH of claim 1; and (b) one or more pharmaceutically acceptable carriers.

17. A method for treating botulism in an individual in need thereof, the method comprising administering, to the individual, a therapeutically effective amount of (a) the single chain antibody binding domain (VHH) of claim 1, or (b) a multimeric VHH construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKS- GIV (SEQ ID NO:15) and CDR3 NVGEF (SEQ ID NO:16) and wherein at least one of the first VHH or the second VHH are the VHH of claim 1.

18. A complex comprising a botulinum neurotoxin bound to (i) the single chain antibody binding domain (VHH) of claim 1 or (ii) a multimeric VHH construct comprising an N-terminal first VHH and a C-terminal second VHH, wherein the first VHH and the second VHH are independently selected from the VHH of claim 1 or a VHH comprising a CDR1 GFGTWFRFDENT (SEQ ID NO:14), CDR2 VARYPKSGIV (SEQ ID NO:15) and CDR3 NVGEF (SEQ ID NO:16) and wherein at least one of the first VHH or the second VHH are the VHH of claim 1.

* * * * *

SEQUENCE LISTING

```
<160> NUMBER OF SEQ ID NOS: 16

<210> SEQ ID NO 1
<211> LENGTH: 125
<212> TYPE: PRT
<213> ORGANISM: Artificial sequence
<220> FEATURE:
<223> OTHER INFORMATION: Synthetic construct

<400> SEQUENCE: 1

Gln Val Gln Leu Val Glu Ser Gly Gly Gly Leu Ala Gln Pro Gly Gly
1               5                   10                  15

Ser Leu Arg Leu Ser Cys Glu Ala Ser Gly Phe Gly Thr Trp Phe Arg
            20                  25                  30

Phe Asp Glu Asn Thr Val Asn Trp Tyr Arg Gln Pro Pro Gly Lys Ser
        35                  40                  45

Arg Glu Phe Asp Glu Leu Val Ala Arg Tyr Pro Lys Ser Gly Ile Val
    50                  55                  60

Thr Tyr Leu Asp Ser Val Lys Gly Arg Phe Thr Ile Ser Arg Asp Asn
65                  70                  75                  80

Ala Lys Lys Met Ala Phe Leu Gln Met Asp Asn Leu Lys Pro Glu Asp
                85                  90                  95

Thr Ala Val Tyr Tyr Cys Asn Val Gly Glu Phe Trp Gly Gln Gly Thr
            100                 105                 110

Gln Val Thr Ile Ser Ser Glu Pro Lys Thr Pro Lys Pro
        115                 120                 125

<210> SEQ ID NO 2
<211> LENGTH: 120
<212> TYPE: PRT
<213> ORGANISM: Artificial sequence
<220> FEATURE:
<223> OTHER INFORMATION: Synthetic construct

<400> SEQUENCE: 2

Gln Val Gln Leu Val Glu Ser Gly Gly Gly Leu Val Gln Val Gly Gly
1               5                   10                  15

Ser Leu Arg Leu Ser Cys Val Val Ser Gly Ser Asp Ile Ser Gly Ile
            20                  25                  30

Ala Met Gly Trp Tyr Arg Gln Ala Pro Gly Lys Arg Arg Glu Met Val
        35                  40                  45

Ala Asp Ile Phe Ser Gly Gly Ser Thr Asp Tyr Ala Gly Ser Val Lys
    50                  55                  60

Gly Arg Phe Thr Ile Ser Arg Asp Asn Ala Lys Lys Thr Ser Tyr Leu
65                  70                  75                  80
```

```
Gln Met Asn Asn Val Lys Pro Glu Asp Thr Gly Val Tyr Tyr Cys Arg
            85                  90                  95

Leu Tyr Gly Ser Gly Asp Tyr Trp Gly Gln Gly Thr Gln Val Thr Val
            100                 105                 110

Ser Ser Ala His His Ser Glu Asp
        115                 120

<210> SEQ ID NO 3
<211> LENGTH: 120
<212> TYPE: PRT
<213> ORGANISM: Artificial sequence
<220> FEATURE:
<223> OTHER INFORMATION: Synthetic construct

<400> SEQUENCE: 3

Gln Val Gln Leu Val Glu Ser Gly Gly Gly Leu Val Gln Val Gly Gly
1               5                   10                  15

Ser Leu Arg Leu Ser Cys Val Val Ser Gly Ser Gly Ile Ser Gly Ile
            20                  25                  30

Ala Met Gly Trp Tyr Arg Gln Ala Pro Gly Lys Arg Arg Glu Met Val
            35                  40                  45

Ala Asp Ile Phe Ser Gly Ser Thr Asp Tyr Ala Gly Ser Val Lys
            50                  55                  60

Gly Arg Phe Thr Ile Ser Arg Asp Asn Ala Lys Lys Thr Ser Tyr Leu
65              70                  75                  80

Gln Met Asn Asn Ala Lys Pro Glu Asp Thr Gly Ala Tyr Tyr Cys Arg
            85                  90                  95

Leu Tyr Gly Ser Gly Asp Tyr Trp Val Gln Gly Thr Gln Val Thr Val
            100                 105                 110

Ser Ser Ala His His Ser Glu Asp
        115                 120

<210> SEQ ID NO 4
<211> LENGTH: 1960
<212> TYPE: PRT
<213> ORGANISM: Artificial sequence
<220> FEATURE:
<223> OTHER INFORMATION: Synthetic construct

<400> SEQUENCE: 4

Gly Ala Gly Ala Thr Ala Thr Ala Cys Cys Ala Thr Gly Gly Ala Ala
1               5                   10                  15

Ala Ala Gly Ala Ala Gly Ala Ala Gly Ala Ala Gly Ala Ala Gly Ala
            20                  25                  30

Ala Ala Ala Ala Gly Ala Ala Ala Ala Ala Ala Gly Gly Gly
            35                  40                  45

Thr Gly Gly Cys Ala Gly Cys Gly Gly Thr Gly Gly Cys Ala Thr Gly
        50                  55                  60

Ala Gly Cys Gly Ala Thr Ala Ala Ala Thr Cys Ala Thr Thr Cys
65              70                  75                  80

Ala Thr Cys Thr Gly Ala Cys Cys Gly Ala Thr Gly Ala Thr Ala Gly
            85                  90                  95

Cys Thr Thr Cys Gly Ala Thr Ala Cys Cys Gly Ala Thr Gly Thr Thr
            100                 105                 110

Cys Thr Gly Ala Ala Gly Cys Ala Gly Ala Thr Gly Gly Thr Gly
        115                 120                 125

Cys Ala Ala Thr Thr Cys Thr Gly Gly Thr Thr Gly Ala Thr Thr Thr
        130                 135                 140
```

```
Thr Thr Gly Gly Gly Cys Ala Gly Ala Ala Thr Gly Gly Thr Gly Thr
145                 150                 155                 160

Gly Gly Thr Cys Cys Gly Thr Gly Thr Ala Ala Ala Ala Thr Gly Ala
                165                 170                 175

Thr Thr Gly Cys Ala Cys Cys Gly Ala Thr Thr Cys Thr Gly Gly Ala
            180                 185                 190

Thr Gly Ala Ala Ala Thr Cys Gly Cys Cys Gly Ala Thr Gly Ala Ala
        195                 200                 205

Thr Ala Thr Cys Ala Gly Gly Gly Thr Ala Ala Ala Cys Thr Gly Ala
    210                 215                 220

Cys Cys Gly Thr Thr Gly Cys Ala Ala Ala Ala Cys Thr Gly Ala Ala
225                 230                 235                 240

Cys Ala Thr Thr Gly Ala Thr Cys Ala Gly Ala Ala Thr Cys Cys Gly
                245                 250                 255

Gly Gly Thr Ala Cys Ala Gly Cys Ala Cys Cys Gly Ala Ala Ala Thr
            260                 265                 270

Ala Thr Gly Gly Thr Ala Thr Thr Cys Gly Thr Gly Gly Thr Ala Thr
        275                 280                 285

Thr Cys Cys Gly Ala Cys Cys Cys Thr Gly Cys Thr Gly Cys Thr Gly
    290                 295                 300

Thr Thr Thr Ala Ala Ala Ala Ala Cys Gly Gly Thr Gly Ala Ala Gly
305                 310                 315                 320

Thr Thr Gly Cys Ala Gly Cys Ala Ala Cys Cys Ala Ala Ala Gly Thr
                325                 330                 335

Thr Gly Gly Thr Gly Cys Ala Cys Thr Gly Ala Gly Cys Ala Ala Ala
            340                 345                 350

Gly Gly Thr Cys Ala Gly Cys Thr Gly Ala Ala Ala Gly Ala Ala Thr
        355                 360                 365

Thr Thr Cys Thr Gly Gly Ala Thr Gly Cys Ala Ala Ala Thr Cys Thr
    370                 375                 380

Gly Gly Cys Ala Gly Gly Thr Ala Gly Cys Gly Gly Thr Ala Gly Cys
385                 390                 395                 400

Gly Gly Thr Cys Ala Thr Ala Thr Gly Cys Ala Thr Cys Ala Thr Cys
                405                 410                 415

Ala Thr Cys Ala Thr Cys Ala Cys Cys Ala Thr Ala Gly Cys Ala Gly
            420                 425                 430

Cys Gly Gly Thr Cys Thr Gly Gly Thr Thr Cys Cys Gly Cys Gly Thr
        435                 440                 445

Gly Gly Thr Ala Gly Cys Gly Gly Thr Ala Thr Gly Ala Ala Ala Gly
    450                 455                 460

Ala Ala Ala Cys Cys Gly Cys Ala Gly Cys Ala Gly Cys Ala Ala Ala
465                 470                 475                 480

Ala Thr Thr Thr Gly Ala Ala Cys Gly Thr Cys Ala Gly Cys Ala Cys
                485                 490                 495

Ala Thr Gly Gly Ala Thr Ala Gly Thr Cys Cys Ala Gly Ala Thr Cys
            500                 505                 510

Thr Gly Gly Gly Cys Ala Cys Cys Gly Ala Thr Gly Ala Thr Gly Ala
        515                 520                 525

Thr Gly Ala Cys Ala Ala Ala Gly Cys Ala Ala Thr Gly Gly Cys Ala
    530                 535                 540

Ala Thr Thr Ala Gly Cys Gly Ala Thr Cys Cys Gly Ala Ala Thr Ala
545                 550                 555                 560
```

-continued

```
Gly Cys Gly Gly Thr Gly Cys Thr Cys Gly Gly Thr Thr Cys Cys
                565                 570                 575
Gly Thr Ala Thr Cys Cys Thr Gly Ala Thr Cys Cys Gly Cys Thr Gly
            580                 585                 590
Gly Ala Ala Cys Cys Gly Cys Gly Thr Gly Cys Ala Gly Cys Ala Gly
        595                 600                 605
Cys Ala Cys Ala Gly Gly Thr Thr Cys Ala Gly Cys Thr Gly Gly Thr
    610                 615                 620
Thr Gly Ala Ala Ala Gly Cys Gly Gly Thr Gly Thr Gly Gly Thr
625                 630                 635                 640
Cys Thr Gly Gly Thr Thr Cys Ala Gly Gly Thr Thr Gly Gly Thr Gly
            645                 650                 655
Gly Thr Ala Gly Cys Cys Thr Gly Cys Gly Thr Cys Thr Gly Ala Gly
        660                 665                 670
Cys Thr Gly Thr Gly Thr Thr Gly Thr Thr Ala Gly Cys Gly Gly Thr
    675                 680                 685
Ala Gly Thr Gly Gly Thr Ala Thr Thr Ala Gly Cys Gly Gly Thr Ala
    690                 695                 700
Thr Thr Gly Cys Ala Ala Thr Gly Gly Thr Thr Gly Gly Thr Ala
705                 710                 715                 720
Thr Cys Gly Thr Cys Ala Gly Gly Cys Ala Cys Cys Gly Gly Thr
            725                 730                 735
Ala Ala Ala Cys Gly Thr Cys Gly Thr Gly Ala Ala Thr Gly Gly
        740                 745                 750
Thr Thr Gly Cys Ala Gly Ala Thr Ala Thr Cys Thr Thr Thr Ala Gly
    755                 760                 765
Cys Gly Gly Thr Gly Gly Thr Ala Gly Cys Ala Cys Ala Gly Ala Thr
    770                 775                 780
Thr Ala Thr Gly Cys Ala Gly Gly Thr Ala Gly Cys Gly Thr Thr Ala
785                 790                 795                 800
Ala Ala Gly Gly Thr Cys Gly Thr Thr Thr Thr Ala Cys Cys Ala Thr
            805                 810                 815
Thr Ala Gly Cys Cys Gly Thr Gly Ala Thr Ala Cys Gly Cys Ala
        820                 825                 830
Ala Ala Ala Ala Ala Ala Cys Cys Ala Gly Cys Thr Ala Thr Cys
    835                 840                 845
Thr Gly Cys Ala Gly Ala Thr Gly Ala Ala Thr Ala Ala Thr Gly Cys
    850                 855                 860
Cys Ala Ala Ala Cys Cys Gly Gly Ala Ala Gly Ala Thr Ala Cys Cys
865                 870                 875                 880
Gly Gly Thr Gly Cys Ala Thr Ala Thr Ala Thr Gly Thr
            885                 890                 895
Gly Thr Cys Thr Gly Thr Ala Thr Gly Gly Thr Ala Gly Thr Gly Gly
        900                 905                 910
Cys Gly Ala Thr Ala Thr Thr Gly Gly Gly Thr Thr Cys Ala Gly
    915                 920                 925
Gly Gly Cys Ala Cys Cys Cys Ala Gly Thr Thr Ala Cys Cys Gly
    930                 935                 940
Thr Thr Ala Gly Cys Ala Gly Cys Gly Cys Ala Cys Ala Thr Cys Ala
945                 950                 955                 960
Thr Ala Gly Cys Gly Ala Ala Gly Ala Thr Cys Cys Gly Ala Cys Cys
            965                 970                 975
Ala Gly Cys Gly Cys Gly Ala Thr Cys Gly Cys Thr Gly Gly Cys Gly
```

-continued

```
                980                985                990
    Gly Thr Gly Gly Thr Gly Gly Thr  Thr Cys Cys Gly Gly  Thr Gly Gly
                995                1000               1005
    Thr Gly Gly Cys Gly Gly Thr  Ala Gly Thr Gly Gly  Thr Gly Gly
            1010               1015               1020
    Thr Gly Gly Thr Gly Gly Cys  Thr Cys Ala Gly Gly  Gly Gly Cys
            1025               1030               1035
    Cys Cys Cys Ala Gly Thr Thr  Cys Cys Gly Thr Ala  Thr Cys Cys
            1040               1045               1050
    Gly Gly Ala Cys Cys Cys Thr  Thr Thr Ala Gly Ala  Ala Cys Cys
            1055               1060               1065
    Thr Cys Gly Cys Gly Cys Thr  Gly Cys Ala Gly Cys  Cys Cys Ala
            1070               1075               1080
    Gly Gly Thr Gly Cys Ala Ala  Cys Thr Gly Gly Thr  Gly Gly Ala
            1085               1090               1095
    Ala Thr Cys Thr Gly Gly Thr  Gly Gly Thr Gly Gly  Cys Cys Thr
            1100               1105               1110
    Gly Gly Thr Gly Cys Ala Ala  Gly Thr Gly Gly Gly  Thr Gly Gly
            1115               1120               1125
    Thr Thr Cys Ala Cys Thr Gly  Cys Gly Thr Cys Thr  Gly Thr Cys
            1130               1135               1140
    Ala Thr Gly Thr Gly Thr Thr  Gly Thr Thr Thr Cys  Ala Gly Gly
            1145               1150               1155
    Thr Thr Cys Ala Gly Gly Thr  Ala Thr Thr Cys Ala  Gly Gly
            1160               1165               1170
    Cys Ala Thr Ala Gly Cys Thr  Ala Thr Gly Gly Cys  Thr Gly
            1175               1180               1185
    Gly Thr Ala Thr Cys Gly Cys  Cys Ala Ala Gly Cys  Cys Cys Cys
            1190               1195               1200
    Thr Gly Gly Cys Ala Ala Ala  Cys Gly Thr Cys Gly  Cys Gly Ala
            1205               1210               1215
    Gly Ala Thr Gly Gly Thr Gly  Gly Cys Cys Gly Ala  Thr Ala Thr
            1220               1225               1230
    Thr Thr Thr Cys Ala Gly Thr  Gly Gly Thr Gly Gly  Thr Thr Cys
            1235               1240               1245
    Ala Ala Cys Cys Gly Ala Thr  Thr Ala Thr Gly Cys  Cys Gly Gly
            1250               1255               1260
    Thr Thr Cys Ala Gly Thr Gly  Ala Ala Ala Gly Gly  Thr Cys Gly
            1265               1270               1275
    Cys Thr Thr Thr Ala Cys Ala  Ala Thr Thr Cys Ala  Cys Gly
            1280               1285               1290
    Thr Gly Ala Cys Ala Ala Thr  Gly Cys Cys Ala Ala  Ala Ala Ala
            1295               1300               1305
    Ala Ala Ala Cys Cys Thr Cys  Ala Thr Ala Cys Cys  Thr Gly Cys
            1310               1315               1320
    Ala Gly Ala Thr Gly Ala Ala  Cys Ala Ala Cys Gly  Cys Ala Ala
            1325               1330               1335
    Ala Ala Cys Cys Thr Gly Ala  Gly Gly Ala Cys Ala  Cys Ala Gly
            1340               1345               1350
    Gly Thr Gly Cys Cys Thr Ala  Thr Thr Ala Cys Thr  Gly Cys Cys
            1355               1360               1365
    Gly Thr Cys Thr Gly Thr Ala  Cys Gly Gly Thr Thr  Cys Ala Gly
            1370               1375               1380
```

-continued

Gly Thr Gly Ala Thr Thr Ala Thr Thr Gly Gly Thr Gly Cys
1385              1390              1395

Ala Ala Gly Gly Thr Ala Cys Thr Cys Ala Gly Thr Gly Ala
1400              1405              1410

Cys Ala Gly Thr Thr Ala Gly Cys Thr Cys Ala Gly Ala Cys Ala
1415              1420              1425

Thr Cys Ala Thr Thr Cys Ala Gly Ala Ala Gly Ala Thr Cys Cys
1430              1435              1440

Thr Ala Cys Cys Thr Cys Ala Gly Cys Ala Ala Thr Thr Gly Cys
1445              1450              1455

Cys Gly Gly Thr Gly Gly Thr Gly Gly Cys Gly Gly Ala Thr Cys
1460              1465              1470

Cys Gly Gly Thr Gly Gly Cys Gly Gly Thr Gly Thr Thr Cys
1475              1480              1485

Thr Gly Gly Cys Gly Gly Thr Gly Gly Thr Gly Thr Thr Cys
1490              1495              1500

Ala Cys Ala Ala Gly Thr Gly Cys Ala Gly Cys Thr Gly Gly Thr
1505              1510              1515

Ala Gly Ala Ala Thr Cys Thr Gly Gly Thr Gly Gly Cys Gly Gly
1520              1525              1530

Thr Cys Thr Gly Gly Cys Ala Cys Ala Gly Cys Cys Thr Gly Gly
1535              1540              1545

Thr Gly Gly Thr Thr Cys Thr Cys Thr Gly Cys Gly Cys Cys Thr
1550              1555              1560

Gly Ala Gly Cys Thr Gly Cys Gly Ala Ala Gly Cys Ala Ala Gly
1565              1570              1575

Cys Gly Gly Thr Thr Thr Thr Gly Gly Cys Ala Cys Cys Thr Gly
1580              1585              1590

Gly Thr Thr Thr Cys Gly Thr Thr Thr Gly Ala Thr Gly Ala
1595              1600              1605

Ala Ala Ala Cys Ala Cys Cys Gly Thr Ala Ala Cys Thr Gly
1610              1615              1620

Gly Thr Ala Thr Cys Gly Thr Cys Ala Ala Cys Cys Gly Cys Cys
1625              1630              1635

Thr Gly Gly Thr Ala Ala Ala Ala Gly Cys Cys Gly Thr Gly Ala
1640              1645              1650

Ala Thr Thr Thr Gly Ala Thr Gly Ala Ala Cys Thr Gly Gly Thr
1655              1660              1665

Thr Gly Cys Ala Cys Gly Thr Thr Ala Thr Cys Cys Gly Ala Ala
1670              1675              1680

Ala Ala Gly Cys Gly Gly Thr Ala Thr Gly Thr Thr Ala Cys
1685              1690              1695

Cys Thr Ala Thr Cys Thr Gly Gly Ala Thr Ala Gly Thr Gly Thr
1700              1705              1710

Gly Ala Ala Ala Gly Gly Cys Cys Gly Thr Thr Thr Cys Ala Cys
1715              1720              1725

Cys Ala Thr Thr Thr Cys Thr Cys Gly Cys Gly Ala Thr Ala Ala
1730              1735              1740

Thr Gly Cys Gly Ala Ala Ala Ala Ala Ala Thr Gly Gly Cys
1745              1750              1755

Ala Thr Thr Cys Cys Thr Gly Cys Ala Gly Ala Thr Gly Gly Ala
1760              1765              1770

```
Thr Ala  Ala Cys Cys Thr Gly  Ala Ala Ala Cys Cys  Thr Gly Ala
    1775                 1780                 1785

Ala Gly  Ala Thr Ala Cys Ala  Gly Cys Cys Gly Thr  Gly Thr Ala
    1790                 1795                 1800

Thr Thr  Ala Thr Thr Gly Cys  Ala Ala Thr Gly Thr  Thr Gly Gly
    1805                 1810                 1815

Thr Gly  Ala Ala Thr Thr Thr  Thr Thr Gly Gly Gly  Gly Thr Cys
    1820                 1825                 1830

Ala Gly  Gly Gly Thr Ala Cys  Thr Cys Ala Gly Gly  Thr Ala Ala
    1835                 1840                 1845

Cys Cys  Ala Thr Thr Ala Gly  Thr Ala Gly Cys Gly  Ala Ala Cys
    1850                 1855                 1860

Cys Gly  Ala Ala Ala Ala Cys  Cys Cys Cys Gly Ala  Ala Ala Cys
    1865                 1870                 1875

Cys Gly  Cys Ala Gly Ala Cys  Cys Ala Gly Thr Gly  Gly Thr Gly
    1880                 1885                 1890

Cys Thr  Cys Cys Gly Gly Thr  Gly Cys Cys Thr Thr  Ala Thr Cys
    1895                 1900                 1905

Cys Ala  Gly Ala Cys Cys Cys  Ala Cys Thr Gly Gly  Ala Ala Cys
    1910                 1915                 1920

Cys Ala  Cys Gly Thr Cys Thr  Cys Gly Ala Gly Ala  Cys Cys Ala
    1925                 1930                 1935

Cys Cys  Ala Cys Cys Ala Cys  Cys Ala Cys Cys Ala  Cys Thr Gly
    1940                 1945                 1950

Ala Gly  Ala Thr Cys Cys Gly
    1955                 1960

<210> SEQ ID NO 5
<211> LENGTH: 8
<212> TYPE: PRT
<213> ORGANISM: Artificial sequence
<220> FEATURE:
<223> OTHER INFORMATION: Synthetic construct
<400> SEQUENCE: 5

Gly Ser Gly Ile Ser Gly Ile Ala
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic construct
<400> SEQUENCE: 6

Ile Phe Ser Gly Gly Ser Thr
1               5

<210> SEQ ID NO 7
<211> LENGTH: 11
<212> TYPE: PRT
<213> ORGANISM: Artificial sequence
<220> FEATURE:
<223> OTHER INFORMATION: Synthetic construct
<400> SEQUENCE: 7

Arg Leu Tyr Gly Ser Gly Asp Tyr Trp Val Gln
1               5                   10
```

```
<210> SEQ ID NO 8
<211> LENGTH: 25
<212> TYPE: PRT
<213> ORGANISM: Artificial sequence
<220> FEATURE:
<223> OTHER INFORMATION: Synthetic construct

<400> SEQUENCE: 8

Gln Val Gln Leu Val Glu Ser Gly Gly Gly Leu Val Gln Val Gly Gly
1               5                   10                  15

Ser Leu Arg Leu Ser Cys Val Val Ser
            20                  25

<210> SEQ ID NO 9
<211> LENGTH: 17
<212> TYPE: PRT
<213> ORGANISM: Artificial sequence
<220> FEATURE:
<223> OTHER INFORMATION: Synthetic construct

<400> SEQUENCE: 9

Met Gly Trp Tyr Arg Gln Ala Pro Gly Lys Arg Arg Glu Met Val Ala
1               5                   10                  15

Asp

<210> SEQ ID NO 10
<211> LENGTH: 35
<212> TYPE: PRT
<213> ORGANISM: Artificial sequence
<220> FEATURE:
<223> OTHER INFORMATION: Synthetic construct

<400> SEQUENCE: 10

Gly Ser Val Lys Gly Arg Phe Thr Ile Ser Arg Asp Asn Ala Lys Lys
1               5                   10                  15

Thr Ser Tyr Leu Gln Met Asn Asn Ala Lys Pro Glu Asp Thr Gly Ala
            20                  25                  30

Tyr Tyr Cys
        35

<210> SEQ ID NO 11
<211> LENGTH: 14
<212> TYPE: PRT
<213> ORGANISM: Artificial sequence
<220> FEATURE:
<223> OTHER INFORMATION: Synthetic construct

<400> SEQUENCE: 11

Gly Thr Gln Val Thr Val Ser Ser Ala His His Ser Glu Asp
1               5                   10

<210> SEQ ID NO 12
<211> LENGTH: 73
<212> TYPE: PRT
<213> ORGANISM: Artificial sequence
<220> FEATURE:
<223> OTHER INFORMATION: Synthetic construct

<400> SEQUENCE: 12

Glu Glu Glu Glu Lys Lys Lys Gln Gln Glu Glu Glu Ala Glu Arg Leu
1               5                   10                  15

Arg Arg Ile Gln Glu Glu Met Glu Lys Glu Arg Lys Arg Arg Glu Glu
            20                  25                  30

Asp Glu Glu Arg Arg Arg Lys Glu Glu Glu Arg Arg Met Lys Leu
```

```
                    35                  40                  45
Glu Met Glu Ala Lys Arg Lys Gln Glu Glu Glu Arg Lys Lys Arg
             50                  55                  60
Glu Asp Asp Glu Lys Arg Lys Lys Lys
65                  70
```

<210> SEQ ID NO 13
<211> LENGTH: 206
<212> TYPE: PRT
<213> ORGANISM: Artificial sequence
<220> FEATURE:
<223> OTHER INFORMATION: Synthetic construct

<400> SEQUENCE: 13

```
Glu Glu Glu Glu Lys Lys Lys Glu Glu Glu Glu Lys Lys Gln Lys Glu
1               5                   10                  15
Glu Gln Glu Arg Leu Ala Lys Glu Glu Ala Glu Arg Lys Gln Lys Glu
                20                  25                  30
Glu Gln Glu Arg Leu Ala Lys Glu Glu Ala Glu Arg Lys Gln Lys Glu
                35                  40                  45
Glu Glu Glu Arg Lys Gln Lys Glu Glu Glu Arg Lys Gln Lys Glu
            50                  55                  60
Glu Glu Glu Arg Lys Leu Lys Glu Glu Gln Glu Arg Lys Ala Ala Glu
65                  70                  75                  80
Glu Lys Lys Ala Lys Glu Ala Glu Arg Lys Ala Lys Glu Glu Gln
                85                  90                  95
Glu Arg Lys Ala Glu Glu Glu Arg Lys Lys Lys Glu Glu Glu Glu Arg
                100                 105                 110
Leu Glu Arg Glu Arg Lys Glu Arg Glu Glu Gln Glu Lys Lys Ala Lys
                115                 120                 125
Glu Glu Ala Glu Arg Ile Ala Lys Leu Glu Ala Glu Lys Lys Ala Glu
            130                 135                 140
Glu Glu Arg Lys Ala Lys Glu Glu Glu Arg Lys Ala Lys Glu Glu
145                 150                 155                 160
Glu Glu Arg Lys Lys Lys Glu Glu Gln Glu Arg Leu Ala Lys Glu Lys
                165                 170                 175
Glu Glu Ala Glu Arg Lys Ala Ala Glu Glu Lys Lys Ala Lys Glu Glu
                180                 185                 190
Gln Glu Arg Lys Glu Lys Glu Glu Ala Glu Arg Lys Gln Arg
                195                 200                 205
```

<210> SEQ ID NO 14
<211> LENGTH: 12
<212> TYPE: PRT
<213> ORGANISM: Artificial sequence
<220> FEATURE:
<223> OTHER INFORMATION: Synthetic construct

<400> SEQUENCE: 14

```
Gly Phe Gly Thr Trp Phe Arg Phe Asp Glu Asn Thr
1               5                   10
```

<210> SEQ ID NO 15
<211> LENGTH: 10
<212> TYPE: PRT
<213> ORGANISM: Artificial sequence
<220> FEATURE:
<223> OTHER INFORMATION: Synthetic construct

<400> SEQUENCE: 15

```
Val Ala Arg Tyr Pro Lys Ser Gly Ile Val
1               5                   10

<210> SEQ ID NO 16
<211> LENGTH: 5
<212> TYPE: PRT
<213> ORGANISM: Artificial sequence
<220> FEATURE:
<223> OTHER INFORMATION: Synthetic construct

<400> SEQUENCE: 16

Asn Val Gly Glu Phe
1               5
```